(12) United States Patent
Bergmann et al.

(10) Patent No.: US 7,786,139 B2
(45) Date of Patent: Aug. 31, 2010

(54) PDE10 INHIBITORS AND RELATED COMPOSITIONS AND METHODS

(75) Inventors: John E. Bergmann, Mercer Island, WA (US); Neil S. Cutshall, Snohomish, WA (US); Rene Onrust, Mercer Island, WA (US); Hongkui Zeng, Shoreline, WA (US); Jennifer Lynn Gage, Kenmore, WA (US); Derek Johnston, Glasgow (GB); Sándor Cseh, Dunakeszi (HU); László Ürögdi, Budapest (HU); Ákos Papp, Budapest (HU)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 12/124,051

(22) Filed: May 20, 2008

(65) Prior Publication Data

US 2008/0300240 A1     Dec. 4, 2008

Related U.S. Application Data

(63) Continuation-in-part of application No. 11/944,270, filed on Nov. 21, 2007, now abandoned.

(60) Provisional application No. 60/866,745, filed on Nov. 21, 2006, provisional application No. 60/896,386, filed on Mar. 22, 2007.

(51) Int. Cl.
*A01N 43/42* (2006.01)
*A61K 31/47* (2006.01)
*C07D 215/00* (2006.01)

(52) U.S. Cl. .................. 514/311; 514/312; 546/152

(58) Field of Classification Search .............. None
See application file for complete search history.

(56) References Cited

U.S. PATENT DOCUMENTS

| 3,847,911 | A | 11/1974 | Szarvasi et al. | 260/240 |
|---|---|---|---|---|
| 3,914,379 | A | 10/1975 | Szarvasi et al. | 424/275 |
| 5,693,652 | A | 12/1997 | Takase et al. | 514/322 |
| 6,323,228 | B1 | 11/2001 | BaMaung et al. | 514/365 |
| 6,350,603 | B1 | 2/2002 | Loughney | 435/196 |
| 6,864,070 | B2 | 3/2005 | Loughney | 435/69.2 |
| 7,268,142 | B2 | 9/2007 | Allen et al. | 514/266.21 |
| 2002/0091414 | A1 | 7/2002 | BaMaung et al. | 514/414 |
| 2003/0008806 | A1 | 1/2003 | Lebel et al. | 514/1 |
| 2003/0018047 | A1 | 1/2003 | Lebel et al. | 514/317 |
| 2003/0032579 | A1 | 2/2003 | Lebel et al. | 514/1 |
| 2003/0044950 | A1 | 3/2003 | Loughney | 435/196 |
| 2003/0148378 | A1 | 8/2003 | Loughney | 435/7.1 |
| 2004/0152106 | A1 | 8/2004 | Robertson et al. | 435/6 |
| 2004/0162293 | A1 | 8/2004 | Lebel et al. | 514/252.16 |
| 2004/0162294 | A1 | 8/2004 | Lebel et al. | 514/252.16 |
| 2005/0009062 | A1 | 1/2005 | Loughney | 435/6 |
| 2005/0043369 | A1 | 2/2005 | Markham et al. | 514/357 |
| 2005/0154056 | A1 | 7/2005 | Yang et al. | 514/518 |
| 2005/0182079 | A1 | 8/2005 | Allen et al. | 514/266.21 |
| 2006/0154931 | A1 | 7/2006 | Verhoest et al. | 514/249 |
| 2006/0217426 | A1 | 9/2006 | Eto et al. | 514/355 |
| 2007/0197594 | A1 | 8/2007 | Hayashibe et al. | 514/319 |
| 2010/0035872 | A1 | 2/2010 | Cutshall et al. | 514/230.5 |

FOREIGN PATENT DOCUMENTS

| EP | 0 259 099 A2 | 3/1988 |
|---|---|---|
| JP | 64-2058 | 1/1989 |
| WO | WO 99/01423 A1 | 1/1999 |
| WO | WO 99/42596 A2 | 8/1999 |
| WO | WO 00/39088 A1 | 7/2000 |
| WO | WO 00/73280 A1 | 12/2000 |
| WO | WO 01/24781 A2 | 4/2001 |
| WO | WO 01/41807 A2 | 6/2001 |
| WO | WO 02/32896 A1 | 4/2002 |
| WO | WO 02/102301 A2 | 12/2002 |
| WO | WO 03/008373 A1 | 1/2003 |
| WO | WO 03/093499 A2 | 11/2003 |
| WO | WO 2004/019932 A1 | 3/2004 |
| WO | WO 2004/094370 A2 | 11/2004 |
| WO | WO 2005/037779 A2 | 4/2005 |

(Continued)

OTHER PUBLICATIONS

Vippagunta, Adv. Drug Del. Rev., 2001, vol. 48, pp. 3-26.*

(Continued)

*Primary Examiner*—Brian-Yong S Kwon
*Assistant Examiner*—Bong-Sook Baek
(74) *Attorney, Agent, or Firm*—Seed IP Law Group PLLC

(57) ABSTRACT

Compounds that inhibit PDE10 are disclosed that have utility in the treatment of a variety of conditions, including (but not limited to) psychotic, anxiety, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette syndrome, schizophrenia, delusional disorders, drug-induced psychosis and panic and obsessive-compulsive disorders. The compounds have the general structure:

(I)

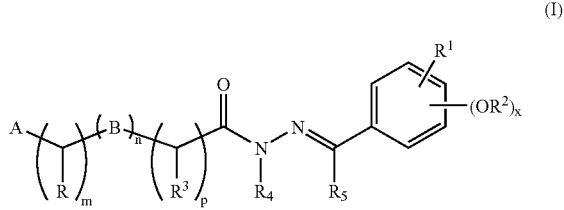

wherein m, n, p, x, R, $R^1$, $R^2$, $R^3$, $R^4$, $R^5$, A and B, are defined herein, including pharmaceutically acceptable salts, stereoisomers, solvates or prodrugs thereof. Also disclosed are compositions containing a compound of this invention in combination with a pharmaceutically acceptable carrier, as well as methods relating to the use thereof for inhibiting PDE10 in a warm-blooded animal in need of the same.

13 Claims, 7 Drawing Sheets

FOREIGN PATENT DOCUMENTS

| | | |
|---|---|---|
| WO | WO 2005/070419 A1 | 8/2005 |
| WO | WO 2005/082883 A2 | 9/2005 |
| WO | WO 2005/097119 A2 | 10/2005 |
| WO | WO 2005/120514 A1 | 12/2005 |
| WO | WO 2005/120515 A2 | 12/2005 |
| WO | WO 2006/028957 A1 | 3/2006 |
| WO | WO 2006/028967 A2 | 3/2006 |
| WO | WO 2006/033318 A1 | 3/2006 |
| WO | WO 2006/113236 A2 | 10/2006 |
| WO | WO 2006/121684 A2 | 11/2006 |
| WO | WO 2006/127396 A1 | 11/2006 |
| WO | WO 2007/008529 A2 | 1/2007 |
| WO | WO 2007/047394 A2 | 4/2007 |
| WO | WO 2008/020920 A1 | 2/2008 |
| WO | WO 2008/064342 A2 | 5/2008 |
| WO | WO 2010/017236 A1 | 2/2010 |

OTHER PUBLICATIONS

Brazhko et al., Medichna Khimiya (2001), 3(1), 20-23.*

Coskran et al., "Immunohistochemical Localization of Phosphodiesterase 10A in Multiple Mammalian Species," *Journal of Histochemistry & Cytochemistry* 54(11):1205-1213, 2006.

Hebb et al., "Role of phosphodiesterases in neurological and psychiatric disease," *Current Opinion in Pharmacology* 7:86-92, 2007.

International Preliminary Report on Patentability, PCT/US2007/085440, dated May 26, 2009 (8 pages).

International Search Report & Written Opinion, PCT/US2007/085440, mailed Jul. 29, 2008 (16 pages).

Kehler et al., "The potential therapeutic use of phosphodiesterase 10 inhibitors," *Expert Opin. Ther. Patents* 17(2):147-158, 2007.

Siuciak et al., "Inhibition of the striatum-enriched phosphodiesterase PDE10A: A novel approach to the treatment of psychosis," *Neuropharmacology* 51:386-396, 2006.

Database Registry Chemical Library, Supplier: Sigma-Aldrich, May 11, 2006, XP002488205, retrieved from STN accession No. RN 883805-25-2, abstract.

Database Registry Chemical Library, Supplier: Sigma-Aldrich, May 11, 2006, XP002488206, retrieved from STN accession No. RN 883826-67-3, abstract.

Dayam et al., "Diketo Acid Pharmacophore. 2. Discovery of Structurally Diverse Inhibitors of HIV-1 Integrase," *Journal of Medicinal Chemistry* 48(25): 8009-8015, 2005.

Fleming et al., "PDE4-regulated cAMP degradation controls the assembly of integrin-dependent actin adhesion structures and REF52 cell migration," *Journal of Cell Science* 117(11):2377-2388, 2004.

Fujishige et al., "Cloning and Characterization of a Novel Human Phosphodiesterase That Hydrolyzes Both cAMP and cGMP (PDE10A)," *The Journal of Biological Chemistry* 274(26):18438-18445, 1999.

Loughney et al., "Isolation and characterization of PDE10A, a novel human 3', 5'-cyclic nucleotide phosphodiesterase," *Gene* 234:109-117, 1999.

Lugnier, C., "Cyclic nucleotide phosphodiesterase (PDE) superfamily: A new target for the development of specific therapeutic agents," *Pharmacology & Therapeutics* 109:366-398, 2006.

Mamolo et al., "Synthesis and antimycobacterial activity of [5-(pyridin-2-yl)-1,3,4-thiadiazol-2-ylthio]acetic acid arylidenehydrazide derivatives," *Il Farmaco* 56:587-592, 2001.

Soderling et al., "Isolation and characterization of a dual-substrate phosphodiesterase gene family: PDE10A," *Proc. Natl. Acad. Sci. USA* 96:7071-7076, Jun. 1999.

Soderling et al., "Regulation of cAMP and cGMP signaling: new phosphodiesterases and new functions," *Current Opinion in Cell Biology* 12:174-179, 2000.

Thompson et al., "Multiple Cyclic Nucleotide Phosphodiesterase Activities from Rat Brain," *Biochemistry* 10(2):311-316, 1971.

Thompson et al., "Characterization of Cyclic Nucleotide Phosphodiesterases of Rat Tissues," *The Journal of Biological Chemistry* 246(10):3145-3150, May 25, 1971.

Bernardino et al., "Synthesis and leishmanicidal activities of 1-(4-X-phenyl)-N'-[(4-Y-phenyl)methylene]-1*H*-pyrazole-4-carbohydrazides," *European Journal of Medicinal Chemistry* 41:80-87, 2006.

da Silva Lourenço et al., "Synthesis and anti-mycobacterial activity of (*E*)-*N*'- (monosubstituted-benzylidene)isonicotinohydrazide derivatives," *European Journal of Medicinal Chemistry* 43:1344-1347, 2008.

de Nardo, M., "Fusaric Acid Derivatives and Analogues As Possible Antihypertensive Drugs. Note II," *Il Farmaco, Edizione Scientifica* 36(4):269-273, Apr. 1981.

de Souza et al., "4-Cyanobenzaldehyde isonicotinoyl-hydrazone monohydrate: a three-dimensional hydrogen-bonded framework structure," *Acta Crystallographica* C63:0166-0168, 2007.

Dias et al., "Synthesis and analgesic properties of 5-acyl-arylhydrazone 1-H pyrazolo [3,4-b] pyridine derivatives," *Pharmaceutica Acta Helvetiae* 69:163-169, 1994.

Fraga et al., "Synthesis and pharmacological evaluation of novel heterotricyclic acylhydrazone derivatives, designed as PAF antagonists," *European Journal of Pharmaceutical Sciences* 11:285-290, 2000.

Hanna et al., "Mechanistic differences between in vitro assays for hydrazone-based small molecule inhibitors of anthrax lethal factor," *Bioorganic Chemistry* 35:50-58, 2007.

Lima et al., "Synthesis and analgesic activity of novel *N*-acylarylhydrazones and isosters, derived from natural safrole," *European Journal of Medicinal Chemistry* 35:187-203, 2000.

Ozaki et al., "Nonlinear Optical Properties of Carbohydrazono-Pyrazole Derivatives with Excellent Transparency," *Japanese Journal of Applied Physics, Part 2*, 31(8A):1068-1070, Aug. 1, 1992.

Ozaki et al., "Second-Order Nonlinear Optical Properties in Hydrazone Derivatives," *Technology Reports of the Osaka University* 42(2109):285-290, Oct. 1992.

Ribeiro et al., "Synthesis and antinociceptive properties of new structurally planned imidazo[1,2-a]pyridine 3-acylarylhydrazone derivatives," *European Journal of Medicinal Chemistry* 33:225-235, 1998.

Sato et al., "Minimal Inhibitory Concentration and Minimal Bactericidal Concentration Determination of Isonicotinic Acid Derivatives Against Mycobacterium Tuberculosis," *Rev. Inst. Adolfo Lutz*, 58(1):25-31, 1999 (+ English abstract).

Šink et al., "Synthesis and Biological Evaluation of *N*-Acylhydrazones as Inhibitors of MurC and MurD Ligases," *ChemMedChem* 3:1362-1370, 2008.

Yue et al, "Synthesis and Characterisation of 5-(4-methoxyphenyl)-1H-pyrazole acyl hydrazones," *Journal of Liaoning Normal University (Natural Science Edition)* 31(1):78-81, Mar. 2008.

Invitation to Pay Additional Fees, and, Where Applicable, Protest Fee; Annex to Form PCT/ISA/206, Communication Relating to the Results of the Partial International Search for PCT/US2009/044556, filed May 19, 2009, 12 pages.

* cited by examiner

PDE10 INHIBITORS AND RELATED COMPOSITIONS AND METHODS

CROSS-REFERENCES TO RELATED APPLICATIONS

This application is a continuation-in-part of U.S. patent application Ser. No. 11/944,270 filed Nov. 21, 2007, which claims the benefit under 35 U.S.C. §119(e) of U.S. Provisional Patent Application No. 60/866,745 filed Nov. 21, 2006 and U.S. Provisional Patent Application No. 60/896,386 filed Mar. 22, 2007. The foregoing applications are incorporated herein by reference in their entireties.

BACKGROUND

1. Technical Field

This invention relates generally to compounds having activity as PDE10 inhibitors, and to compositions containing the same, as well as to methods of treating various disorders by administration of such compounds to a warm-blooded animal in need thereof.

2. Description of the Related Art

Cyclic nucleotide phosphodiesterases (PDEs) are represented by a large superfamily of enzymes. PDEs are known to possess a modular architecture, with a conserved catalytic domain proximal to the carboxyl terminus, and regulatory domains or motifs often near the amino terminus. The PDE superfamily currently includes more than twenty different genes subgrouped into eleven PDE families (Lugnier, C., "Cyclic nucleotide phosphodiesterase (PDE) superfamily: a new target for the development of specific therapeutic agents." Pharmacol Ther. 2006 March; 109(3):366-98).

A recently described PDE, PDE10, was reported simultaneously by three independent groups (Fujishige et al., "Cloning and characterization of a novel human phosphodiesterase that hydrolyzes both cAMP and cGMP (PDE10A)," *J Biol Chem* 1999, 274:18438-18445; Loughney et al., "Isolation and characterization of PDE10A, a novel human 3',5'-cyclic nucleotide phosphodiesterase," *Gene* 1999, 234:109-117; Soderling et al., "Isolation and characterization of a dual-substrate phosphodiesterase gene family: PDE10A," *Proc Natl Acad Sci USA* 1999, 96:7071-7076). PDE10 has the capacity to hydrolyze both cAMP and cGMP; however, the $K_m$ for cAMP is approximately 0.05 μM, whereas the $K_M$ for cGMP is 3 μM. In addition, the $V_{max}$ for cAMP hydrolysis is fivefold lower than for cGMP. Because of these kinetics, cGMP hydrolysis by PDE10 is potently inhibited by cAMP in vitro, suggesting that PDE10 may function as a cAMP-inhibited cGMP phosphodiesterase in vivo. Unlike PDE8 or PDE9, PDE10 is inhibited by IBMX with an $IC_{50}$ (50% inhibitory concentration) of 2.6 μM. (See Soderling and Beavo, "Regulation of cAMP and cGMP signaling: new phosphodiesterases and new functions," *Current Opinion in Cell Biology*, 2000, 12:174-179.)

PDE10 contains two amino-terminal domains that are similar to the cGMP-binding domains of PDE2, PDE5 and PDE6, which are domains conserved across a wide variety of proteins. Because of the wide conservation of this domain, it is now referred to as the GAF domain (for the GAF proteins: cGMP binding phosphodiesterases; the cynobacterial *Anabaena* adenylyl cyclase; and the *Escherichia coli* transcriptional regulator fhlA). Although in PDE2, PDE5 and PDE6 the GAF domains bind cGMP, this is probably not the primary function of this domain in all cases (e.g., *E. coli* are not thought to synthesize cGMP). Interestingly, in vitro binding studies of PDE10 indicate the dissociation constant ($K_d$) for cGMP binding is well above 9 μM. As in vivo concentrations of cGMP are not thought to reach such high levels in most cells, it seems likely that either the affinity of PDE10 for cGMP is increased by regulation, or that the primary function of the GAF domain in PDE10 may be for something other than cGMP binding.

Inhibitors of the PDE family of enzymes have widely been sought for a broad indication of therapeutic uses. Reported therapeutic uses of PDE inhibitors include allergies, obstrusive lung disease, hypertension, renal carcinoma, angina, congestive heart failure, depression and erectile dysfunction (WO 01/41807 A2). Other inhibitors of PDE have been disclosed for treatment of ischemic heart conditions (U.S. Pat. No. 5,693,652). More specifically, inhibitors of PDE10 have been disclosed for treatment of certain neurological and psychiatric disorders including, Parkinson's disease, Huntington's disease, schizophrenia, delusional disorders, drug-induced psychosis and panic and obsessive-compulsive disorders (U.S. Patent Application No. 2003/0032579). PDE10 has been shown to be present at high levels in neurons in areas of the brain that are closely associated with many neurological and psychiatric disorders. By inhibiting PDE10 activity, levels of cAMP and cGMP are increased within neurons, and the ability of these neurons to function properly is thereby improved. Thus, inhibition of PDE10 is believed to be useful in the treatment of a wide variety of conditions or disorders that would benefit from increasing levels of cAMP and cGMP within neurons, including those neurological, psychotic, anxiety and/or movement disorders mentioned above.

While advances have been made with regard to inhibition of PDE10, there remains a need in the field for inhibitors of PDE10, as well as the need to treat various conditions and/or disorders that would benefit from the same.

BRIEF SUMMARY

In brief, this invention is generally directed to compounds that have activity as PDE10 inhibitors, as well as to methods for their preparation and use, and to pharmaceutical compositions containing the same. More specifically, the compounds of this invention have the following general structure (I):

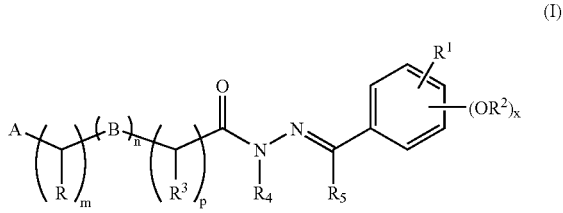

(I)

including pharmaceutically acceptable salts, stereoisomers, solvates and prodrugs thereof, wherein A, B, m, n, p, x, R, $R^1$, $R^2$, $R^3$, $R^4$ and $R^5$ are as defined below.

The compounds of this invention have utility over a wide range of therapeutic applications, and may be used to treat a wide variety of conditions or disorders that would benefit from increasing levels of cAMP and cGMP, especially within neurons, including (but not limited to) psychotic disorders, anxiety disorders, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, cognitive disorders, epilepsy, insomnias and multiple sclerosis.

The methods of this invention include administering an effective amount of a compound of structure (I), typically in the form of a pharmaceutical composition, to a mammal in need thereof, including a human. Thus, in still a further embodiment, pharmaceutical compositions are disclosed containing one or more compounds of structure (I) in combination with a pharmaceutically acceptable carrier or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

FIG. 1A shows that olanzapine (3 mg/kg) significantly decreases the startle response (left panel) and increases PPI at 3 different prepulse levels (right panel) compared to vehicle control (* $p<0.05$, n=8 per group, student's t-test). FIG. 1B shows that compound 5-1 (50 mg/kg) does not affect the startle response (left panel) but significantly increases PPI at 3 different prepulse levels (right panel) compared to vehicle control (* $p<0.05$, ** $p<0.01$, n=24 per group, student's t-test).

FIG. 2A shows that both olanzapine (0.2 mg/kg) and haloperidol (0.2 mg/kg) significantly reduce the hyperactivity (left panel) and stereotypy (right panel) induced by PCP as seen in the vehicle+PCP control ($p<0.001$, n=8 per group, repeated measures ANOVA). FIG. 2B shows that compound 5-1 (50 mg/kg) completely abolishes the hyperactivity (left panel) and stereotypy (right panel) induced by PCP as seen in the vehicle+PCP control ($p<0.001$, n=8 per group, repeated measures ANOVA).

FIG. 3A shows that olanzapine (0.2 mg/kg) partially but significantly reduce the hyperactivity (left panel) and stereotypy (right panel) induced by amphetamine ("amph") as seen in the vehicle+amph control ($p<0.05$, n=8 per group, repeated measures ANOVA). FIG. 3 B shows that compound 5-1 (50 mg/kg) also partially but significantly reduce the hyperactivity (left panel) and stereotypy (right panel) induced by amphetamine as seen in the vehicle+amph control ($p<0.01$, n=8 per group, repeated measures ANOVA).

FIG. 4A shows that haloperidol (0.15 mg/kg) significantly reduces the number of avoidance response (* $p<0.001$, n=6 per group, paired t-test). FIG. 4B shows that olanzapine (0.45 mg/kg) significantly reduces the number of avoidance response ( $p<0.01$, n=6 per group, paired t-test). FIG. 4C shows that compound 5-1 (30 mg/kg) significantly reduces the number of avoidance response (*** $p<0.001$, n=6 per group, paired t-test). In all these cases, the numbers of escape response increase correspondingly and the total numbers of transitions between the two chambers do not change (data not shown), indicating a specific reduction of CAR that is not due to compromised motor function.

FIG. 5A shows that compound 5-110 (10 mg/kg) significantly reduces the number of avoidance response in the CAR test (** $p<0.01$, n=6 per group, paired t-test). FIG. 5B shows that compound 5-110 (30 mg/kg) significantly reduces the hyperactivity (left panel) and stereotypy (right panel) induced by PCP (5 mg/kg) ($p<0.001$, n=8 per group, repeated measures ANOVA).

DETAILED DESCRIPTION

Figure 1:
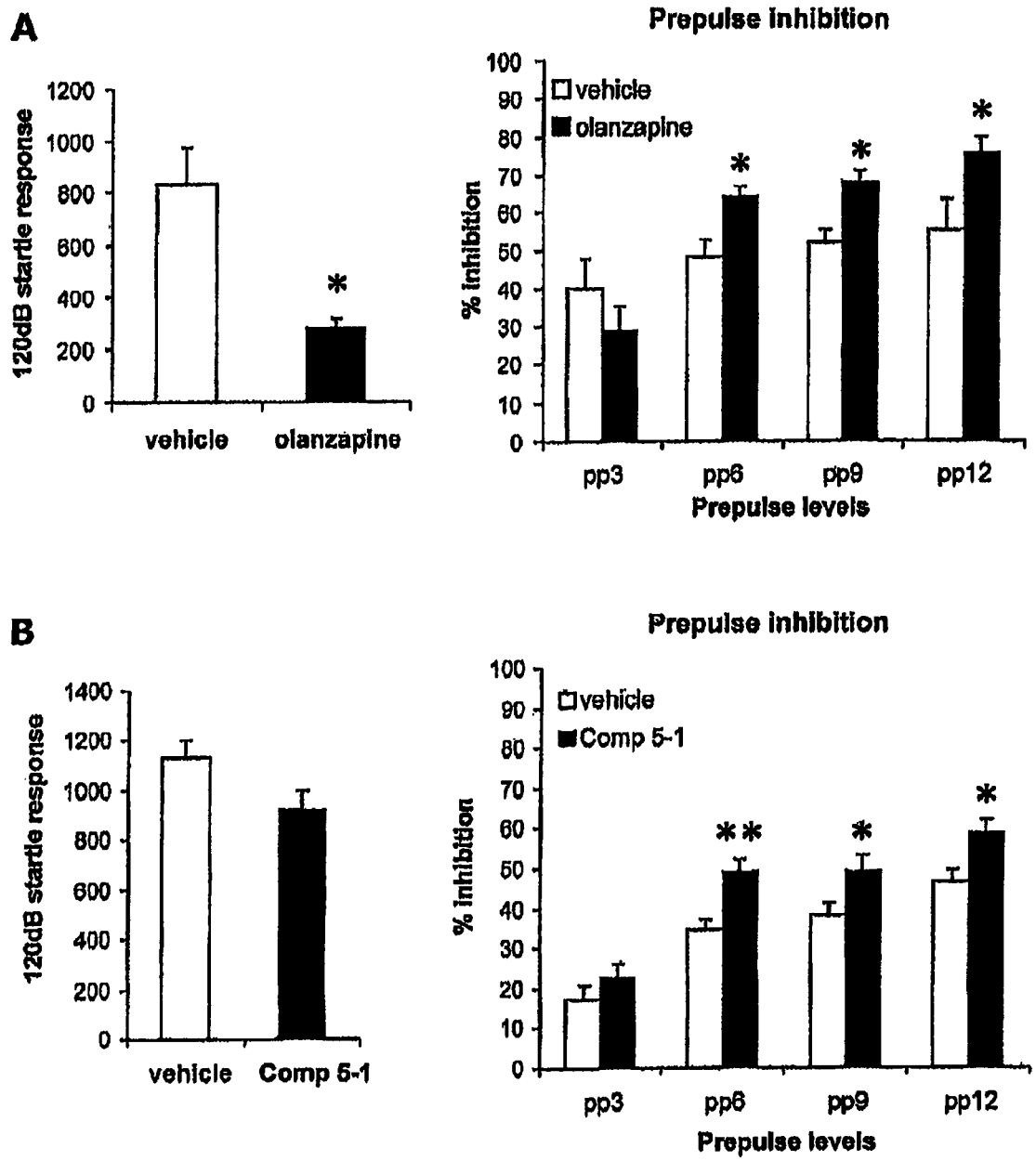
FIG. 1 illustrates that compound 5-1 (Table 3) increases prepulse inhibition (PPI) similar to olanzapine. C57BL/6 male mice were injected intraperitoneally (i.p.) with either compound or vehicle as described in Example 9.

As mentioned above, the present invention is directed generally to compounds useful as PDE10 inhibitors, as well as to methods for their preparation and use, and to pharmaceutical compositions containing the same. The PDE10 inhibitors of this invention have the following structure (I):

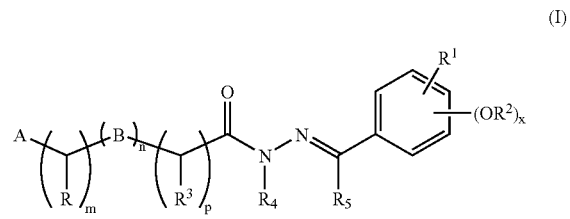

or a pharmaceutically acceptable salt, stereoisomer, solvate or prodrug thereof, wherein:
m, n and p are individually 0 or 1;
x is 1, 2 or 3;
A is an optionally substituted heterocycle;
B is —O—, —NR$^6$— or —S(O)$_z$— where z is 0, 1 or 2;
R is hydrogen or oxo;
R$^1$ is absent or represents 1, 2 or 3 substituents that are the same or different and independently halogen, C$_{1-6}$alkyl, —CHF$_2$, —CF$_3$, —CH$_2$NH$_2$, —CH$_2$NH (C$_{1-6}$alkyl) or —CH$_2$N(C$_{1-6}$alkyl)$_2$;
R$^2$ is at each occurrence the same or different and independently, hydrogen, C$_{1-6}$alkyl, —C(=O)(C$_{1-6}$ alkyl), benzyl, —CH$_2$CONH$_2$, —CHF$_2$, —CF$_3$, or any two R$^2$ groups, or any R$^2$ group and R$^1$ group, may be taken together to form a C$_{1-6}$alkanediyl; and
R$^3$, R$^4$, R$^5$ and R$^6$ are the same or different and independently hydrogen or C$_{1-6}$alkyl.

As used herein, the above terms have the following meaning:

"C$_{1-6}$alkyl" means a straight chain or branched, noncyclic or cyclic, unsaturated or saturated aliphatic hydrocarbon containing from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{1-6}$alkanediyl" means a divalent $C_{1-6}$alkyl from which two hydrogen atoms are taken from the same carbon atom or from different carbon atoms, such as —$CH_2$—, —$CH_2CH_2$—, —CH=CH—, —CH=C($CH_3$)—, —$CH_2CH_2CH_2$—, —$CH_2$CH=CH—, —CH($CH_3$)$CH_2CH_2$—, —$CH_2$C($CH_3$)$_2CH_2$—, and the like.

"Heterocycle" means a 4- to 7-membered monocyclic, or 7- to 10-membered bicyclic, heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. An aromatic heterocycle is referred to herein as a "heteroaryl", and includes (but is not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, oxadiazolyl, thiadiazolyl, benzisoxazolyl, triazolyl, tetrazolyl, indazolyl and quinazolinyl. In addition to the heteroaryls listed above, heterocycles also include morpholinyl, pyrrolidinonyl, pyrrolidinyl, piperidinyl, piperazinyl, and the like.

The term "optionally substituted" as used in the context of an optionally substituted heterocycle (as well heteroaryl) means that at least one hydrogen atom is replaced with a substituent. In the case of an oxo substituent ("=O") two hydrogen atoms are replaced. When substituted, one or more of the above groups are substituted. "substituents" within the context of this invention include halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as —$NR_aR_b$, —$NR_aC(=O)R_b$, —$NR_aC(=O)NR_aR_b$, —$NR_aC(=O)OR_b$, —$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2OR_a$. In addition, the above substituents may be further substituted with one or more of the above substituents, such that the substituent is a substituted alkyl, substituted aryl, substituted arylalkyl, substituted heterocycle or substituted heterocyclealkyl. $R_a$ and $R_b$ in this context may be the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

In one embodiment, both m and n are 0 and p is 1, and the compounds have the following structure (II) or a pharmaceutically acceptable salt, stereoisomer, solvate or prodrug thereof:

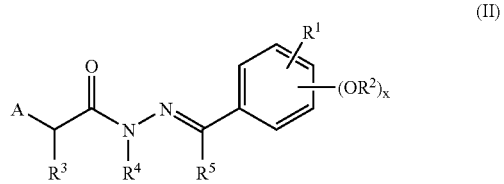

(II)

In another embodiment, m, n and p are 1, and the compounds have the following structure (III) or a pharmaceutically acceptable salt, stereoisomer, solvate or prodrug thereof:

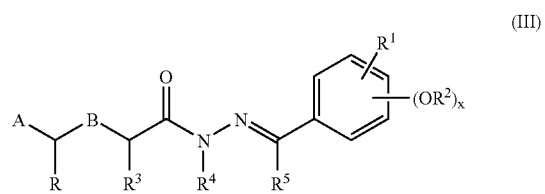

(III)

In another embodiment, m is 0 and n and p are both 1, and the compounds have the following structure (IV) or a pharmaceutically acceptable salt, stereoisomer, solvate or prodrug thereof:

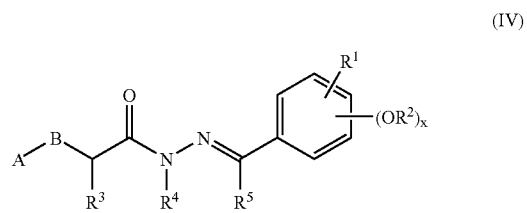

(IV)

In another embodiment, both m and p are 1 and n is 0, and the compounds have the following structure (V) or a pharmaceutically acceptable salt, stereoisomer, solvate or prodrug thereof:

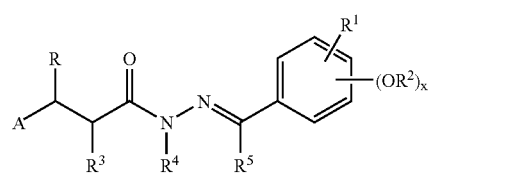

(V)

In another embodiment, each of m, n and p are 0, and the compounds have the following structure (VI) or a pharmaceutically acceptable salt, stereoisomer, solvate or prodrug thereof:

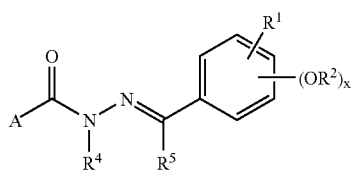
(VI)

In more specific embodiments of structure (II), $R^3$, $R^4$ and $R^5$ are hydrogen.

In other more specific embodiments of structure (II), $R^2$ is methyl or difluoromethyl.

In other more specific embodiments of structure (II), $R^1$ is absent and x is 3 with the $R^2$ groups at the 3, 4 and 5 positions, as represented by structure (IIa):

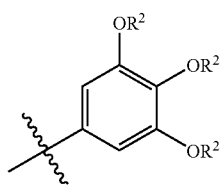
(IIa)

In yet further specific embodiments of structure (II), A is 1H-indol-3-yl or 2H-benzo[b][1,4]thiazin-3(4H)-one-2-yl.

In more specific embodiments of structure (IV), B is —S—, —O— or —NR$^6$—, respectively, and compounds have the following structures (IVa), (IVb) and (IVc):

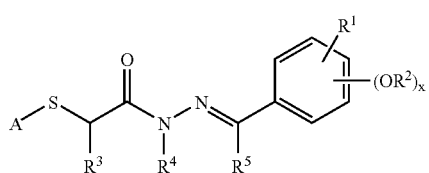
(IVa)

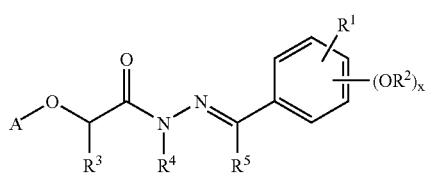
(IVb)

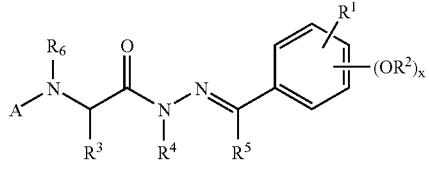
(IVc)

In more specific embodiments of structures (IVa), (IVb) and (IVc), $R^3$, $R^4$, $R^5$ and $R^6$ are hydrogen.

In other more specific embodiments of structures (IVa), (IVb) and (IVc), $R^2$ is hydrogen, methyl, ethyl, difluoromethyl, 2-propenyl, 2-methylpropyl, $C_1$alkanediyl, —CH$_2$CONH$_2$. In yet further specific embodiments, $R^2$ is methyl.

In other more specific embodiments of structures (IVa), (IVb) and (IVc), $R^1$ is absent or halogen, x is 2 with the $R^2$ groups located at the 3 and 4 positions, or x is 3 with the $R^2$ groups located at the 3, 4 and 5 positions, as represented by structures (IVd) and (IVe), respectively:

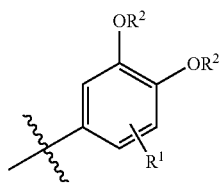
(IVd)

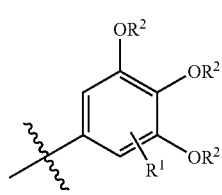
(IVe)

In other more specific embodiments of structures (IVa), (IVb) and (IVc), $R^1$ is 2 substituents that are the same or different and independently halogen, such as fluorine, as represented by structure (IVf):

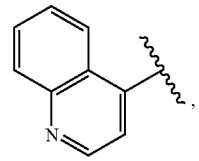
(IVf)

In other more specific embodiments of structures (IVa), (IVb) and (IVc), A is

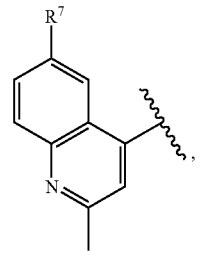

x is 3 and the —OR$^2$ groups are located at the 3, 4 and 5 positions, $R^1$ is absent, $R^2$ is at each occurrence the same or different and independently hydrogen, $C_{1-6}$alkyl, —C(=O) ($C_{1-6}$alkyl), benzyl, —CH$_2$CONH$_2$, —CHF$_2$ or —CF$_3$, and $R^3$, $R^4$ and $R^5$ are hydrogen. In yet further specific embodiments, $R^2$ is at each occurrence the same or different and independently, $C_{1-6}$alkyl or —CHF$_2$ or —CF$_3$.

In other more specific embodiments of structures (IVa), (IVb) and (IVc), A is x is 2 or 3 and two of the —OR² groups are located at the 3 and 4 positions, R¹ is absent, R² is at each occurrence the same or different and independently $C_{1-6}$alkyl, —CHF₂ or —CF₃, R³, R⁴ and R⁵ are hydrogen, and R⁷ is —O($C_{1-6}$alkyl).

In yet further specific embodiments of structure (IVa), A is an optionally substituted quinolin-4-yl as represented by structure (IVg) where a is 1, 2, 3 or 4, b is 1 or 2 and R⁷ and R⁸ are the same or different and independently hydrogen, halogen, $C_{1-6}$alkyl, —O($C_{1-6}$alkyl), $C_{1-6}$haloalkyl or nitro.

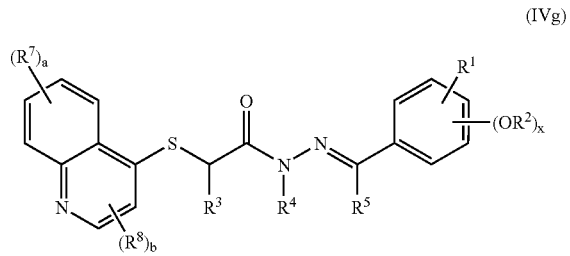

(IVg)

In further specific embodiments of structure (IVg), x is 1 with the proviso that R¹ is not hydrogen or methyl.

In other further specific embodiments of structure (IVg), x is 2 or 3 with the proviso that R¹ is not hydrogen.

In other further specific embodiments of structure (IVg), x is at least one and R¹ and R² are taken together to form —CH═C(CH₃)—.

In other further specific embodiments of structure (IVg), x is 1, 2 or 3, a is 1, b is 0, R¹ is absent or represents 1, 2, or 3 substituents that are the same or different and independently halogen, $C_{1-6}$alkyl, —CHF₂, —CF₃, —CH₂NH₂, —CH₂NH($C_{1-6}$alkyl) or —CH₂N($C_{1-6}$alkyl)₂, R² is at each occurrence the same or different and independently hydrogen, $C_{1-6}$alkyl, —C(═O)($C_{1-6}$alkyl), benzyl, —CH₂CONH₂, —CHF₂ or —CF₃, R³, R⁴ and R⁵ are hydrogen, and R⁷ is halogen or $C_{1-6}$haloalkyl. In yet further specific embodiments, R² is at each occurrence the same or different and independently $C_{1-6}$alkyl, —CHF₂ or —CF₃. In yet further specific embodiments, R¹ is absent or represents 1, 2, or 3 substituents that are the same or different and independently halogen, $C_{1-6}$alkyl, —CHF₂ or —CF₃.

In other further specific embodiments of structure (IVg), a is 1, 2, 3 or 4, b is 1 or 2, x is 1, 2 or 3 with the proviso that when x is 1, R¹ is not a single methyl substituent, R¹ represents 1 or 2 substitutents independently halogen, $C_{1-6}$alkyl, —CHF₂ or —CF₃, R² is at each occurrence the same or different and independently, hydrogen, $C_{1-6}$alkyl, benzyl, —CH₂CONH₂, —CHF₂, —CF₃, or any two R groups may be taken together to form a $C_{1-6}$alkanediyl, R³, R⁴ and R⁵ are the same or different and independently hydrogen or $C_{1-6}$alkyl, and R⁷ and R⁸ are the same or different and independently hydrogen, halogen, $C_{1-6}$alkyl, —O($C_{1-6}$alkyl), $C_{1-6}$haloalkyl or nitro. In yet further specific embodiments, R³, R⁴ and R⁵ are hydrogen. In yet further specific embodiments, R⁷ is hydrogen, R⁸ is —CH₃, a is 1, b is 1 and the compound has the following structure:

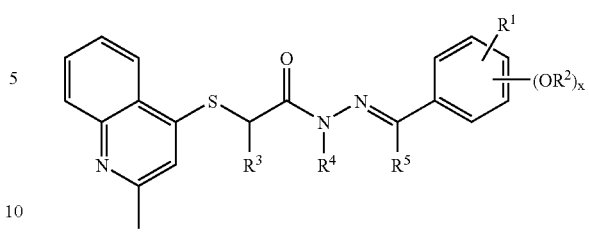

In other further specific embodiments of structure (IVa), A is 2-methylquinolyn-4-yl, quinolin-4-yl, 2-methyl-6-nitroquinolin-4-yl, 6-bromoquinolin-4-yl, 8-methoxy-5-methylquinolin-4-yl, 6,7-dimethoxy-2-methylquniolin-4-yl, 8-methoxyquinolin-4-yl, 7-(trifluoromethyl)quinolin-4-yl, 2-methyl-8-(trifluoromethyl)quinolin-4-yl or 6-methoxyquinolin-4-yl.

In yet further specific embodiments of structure (IVa), A is an optionally substituted 1-benzyl-1H-benzo[d]imidazol-2-yl as represented by structure (IVh) where c is 1, 2, 3, 4 or 5 and R⁹ is hydrogen or halogen.

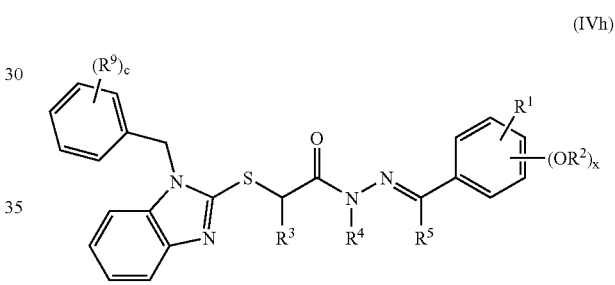

(IVh)

In other further specific embodiments of structure (IVh), c is 1, 2, 3, 4 or 5, x is 1, 2 or 3, R¹ is absent or represents 1 or 2 halogens, R² is at each occurrence the same or different and independently, hydrogen, $C_{1-6}$alkyl, benzyl, —CH₂CONH₂, —CHF₂, or any two R² groups may be taken together to form a $C_{1-6}$alkanediyl, R³, R⁴ and R⁵ are the same or different and independently hydrogen or $C_{1-6}$alkyl, and R⁹ is at each occurrence the same or different and independently, hydrogen or halogen. In yet further specific embodiments, R³, R⁴ and R⁵ are hydrogen. In yet further specific embodiments, c is 1 and R⁹ is hydrogen or chlorine.

In other further specific embodiments of structure (IVh), A is 1-benzyl-1H-benzo[d]imidazol-2-yl, 1-(2-chlorobenzyl)-1H-benzo[d]imidazol-2-yl or 1-(4-chlorobenzyl)-1H-benzo[d]imidazol-2-yl.

In more specific embodiments of structures (I) through (VI) above, any two two R² groups, or any R² group and R¹ group, may be taken together to form a $C_{1-6}$alkanediyl. For example, when two R² groups are taken together to form a $C_{1-6}$alkanediyl (such as —CH₂—) representative compounds have the following structure (1-1), and when an R² group and R¹ group are taken together to form a $C_{1-6}$alkanediyl (such as —CH═C(CH₃)—) representative compounds have the following structure (1-2):

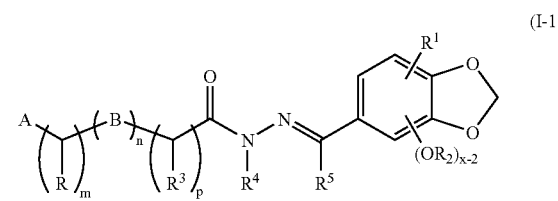

(I-1)

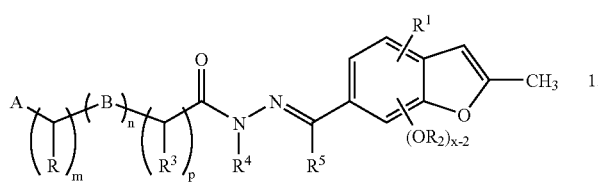

(I-2)

The compounds of the present invention may be prepared by known organic synthesis techniques, including the methods described in more detail in the Examples, or in some instances may be obtained from commercially available sources. In general, the compounds of structure (I) above may be made by the following reaction schemes, wherein all substituents are as defined above unless indicated otherwise.

Reaction Scheme 1

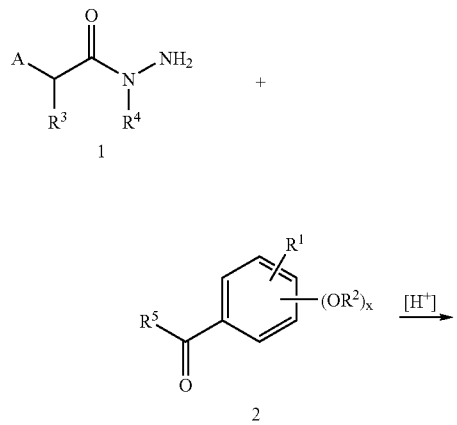

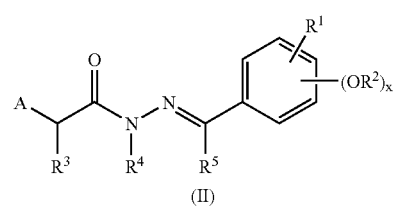

(II)

Compounds of formula (1) can be obtained commercially or synthesized through standard literature methods. Compounds of formula (1) can be reacted with a variety of benzaldehyde derivatives of formula (2) in alcoholic solvents, such as ethanol, and in the presence of a catalytic amount of acid, such as acetic acid, and under reflux to provide compounds of structure (II).

Reaction Scheme 2

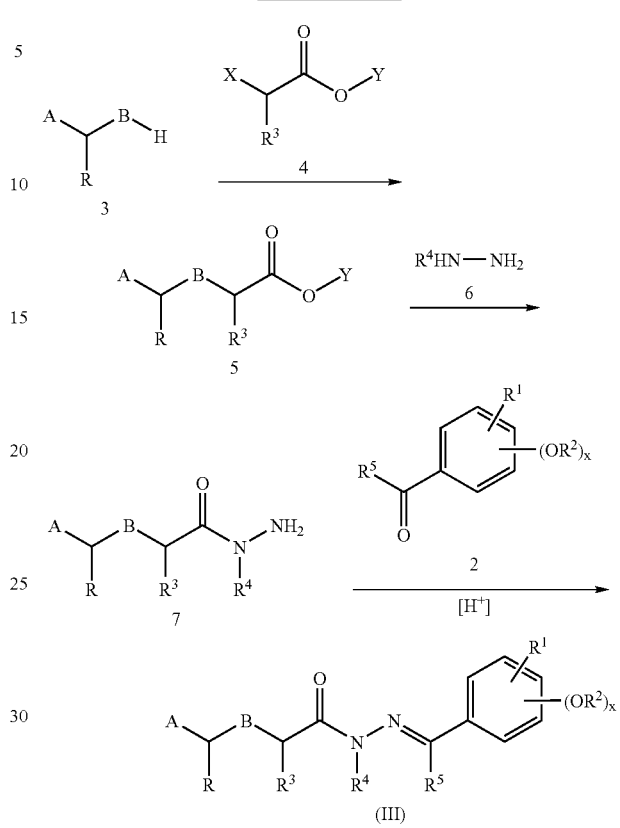

Compounds of formula (3) can be prepared by standard methods or purchased commercially and reacted with compounds of formula (4) where X=Br, Cl and the like, and Y=Me, Et and the like in an appropriate alcoholic solvent such as ethanol and in the presence of a base, such as potassium carbonate and heated to reflux to provide compounds of formula (5). Compounds of formula (5) in ethanol can then be reacted with a hydrazine compound, such as (6), at reflux to provide compounds of formula (7). Compounds of formula (7) can then be reacted with a variety of aryl carbonyl derivatives of formula (2) in alcoholic solvents, such as ethanol, and in the presence of a catalytic amount of acid, such as acetic acid, and under reflux to provide compounds of structure (III).

Reaction Scheme 3

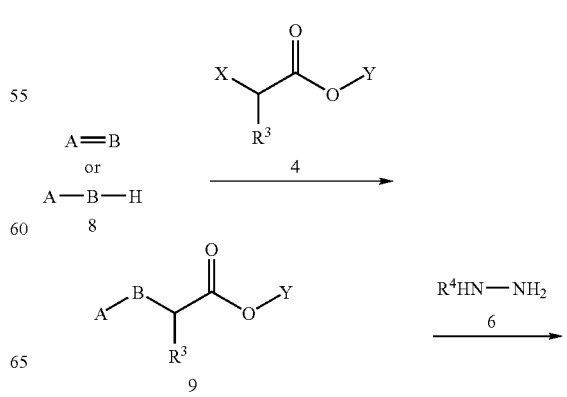

-continued

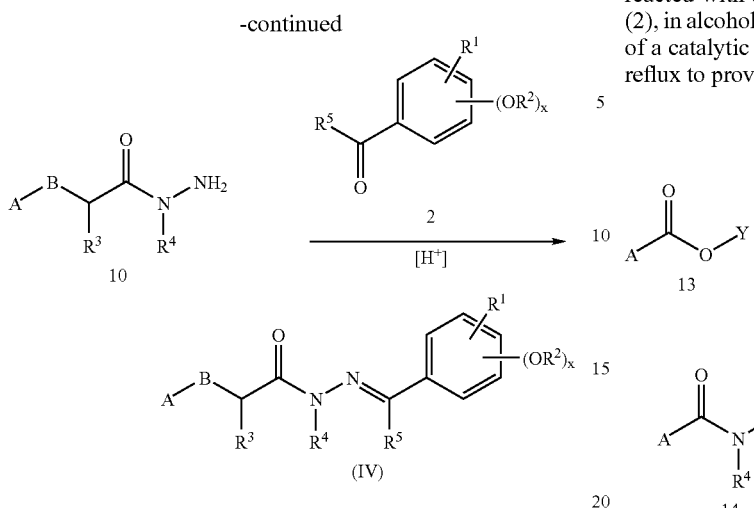

(IV)

Compounds of formula (8) can be purchased commercially or prepared via standard methods. As shown in Scheme 3, compounds of formula (8) can be reacted with compounds of formula (4) where X=Br, Cl and the like and Y=Me, Et and the like in an appropriate alcoholic solvent, such as ethanol, and in the presence of a base, such as potassium carbonate, and heated to reflux to provide compounds of formula (9). Compounds of formula (9) in ethanol can then be reacted with a hydrazine compound, such as (6), at reflux to provide compounds of formula (10). Compounds of formula (10) can then be reacted with a variety of aryl carbonyl derivatives of formula (2) in alcoholic solvents, such as ethanol, and in the presence of a catalytic amount of acid, such as acetic acid, and under reflux to provide compounds of structure (IV).

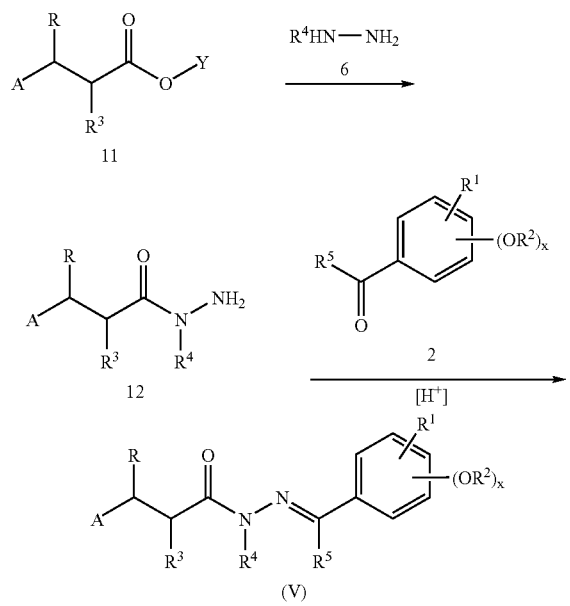

Compounds of formula (11) where Y=Me, Et, and the like can be obtained commercially or prepared via standard methods. Compounds of formula (11) in ethanol can be reacted with a hydrazine compound such as (6) to obtain compounds of formula (12). Compounds of formula (12) can then be reacted with a variety of benzaldehyde derivatives, such as (2), in alcoholic solvents, such as ethanol, and in the presence of a catalytic amount of acid, such as acetic acid, and under reflux to provide compounds of structure (V).

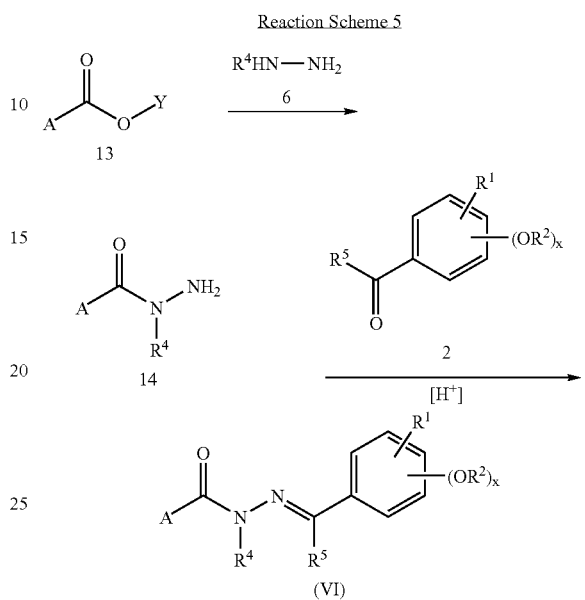

Compounds of formula (13) where Y=methyl (Me), ethyl (Et), etc. can be obtained commercially or prepared via standard methods. Compounds of formula (13) in ethanol can be reacted with a hydrazine compound, such as (6), to obtain compounds of formula (14). Compounds of formula (14) can then be reacted with a variety of benzaldehyde derivatives, such as (2), in alcoholic solvents, such as ethanol, and in the presence of a catalytic amount of acid, such as acetic acid, and under reflux to provide compounds of structure (VI).

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structures (I) through (VI) is intended to encompass any and all acceptable salt forms.

In addition, prodrugs are also included within the context of this invention. Prodrugs are any covalently bonded carriers that release a compound of structures (I) through (VI) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structures (I) through (VI). Further, in the case of a carboxylic acid (—COOH), esters may be employed, such as methyl esters, ethyl esters, and the like.

With regard to stereoisomers, the compounds of structures (I) through (VI) may have chiral centers and may occur as racemates, racemic mixtures and as individual enantiomers or diastereomers. All such isomeric forms are included within the present invention, including mixtures thereof. Furthermore, some of the crystalline forms of the compounds of structures (I) through (VI) may exist as polymorphs, which are included in the present invention. In addition, some of the compounds of structures (I) through (VI) may also form solvates with water or other organic solvents. Such solvates are similarly included within the scope of this invention.

In another embodiment of the invention, pharmaceutical compositions containing one or more compounds of structures (I) through (VI) are disclosed. For the purposes of administration, the compounds of the present invention may be formulated as pharmaceutical compositions. Pharmaceutical compositions of the present invention comprise one or more compounds of the present invention and a pharmaceutically acceptable carrier and/or diluent. The PDE10 inhibitor is present in the composition in an amount which is effective to treat a particular disorder—that is, in an amount sufficient to achieve desired PDE10 inhibition, and preferably with acceptable toxicity to the warm-blooded animal. Typically, the pharmaceutical compositions of the present invention may include a PDE10 inhibitor in an amount from 0.1 mg to 250 mg per dosage depending upon the route of administration, and more typically from 1 mg to 60 mg. Appropriate concentrations and dosages can be readily determined by one skilled in the art.

In general terms, a typical daily dosage might range from about 1 µg/kg to 100 mg/kg, preferably 0.01-100 mg/kg, more preferably 0.1-70 mg/kg, depending on the type and severity of the disease whether, for example, by one or more separate administrations. For repeated administrations over several days or longer, depending on the condition, the treatment is sustained until a desired suppression of disease symptoms occurs. However, other dosage regimens may be useful. The progress of this therapy can be monitored by standard techniques and assays. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a PDE10 inhibitor, diluents, dispersing and surface active agents, binders, and lubricants. One skilled in this art may further formulate the PDE10 inhibitor in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating diseases such as (but not limited to) psychotic disorders, anxiety disorders, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, cognitive disorders, epilepsy, insomnias and multiple sclerosis as discussed above. Such methods include administering of a compound of the present invention to a warm-blooded animal in an amount sufficient to treat the condition. In this context, "treat" includes prophylactic administration. Such methods include systemic administration of a PDE10 inhibitor of this invention, preferably in the form of a pharmaceutical composition as discussed above. As used herein, systemic administration includes oral and parenteral methods of administration, including subcutaneous, intramuscular, intracranial, intraorbital, ophthalmic, intraventricular, intracapsular, intraarticular, intraspinal, intracisternal, intraperitoneal, intranasal, aerosol, intravenous, intradermal, inhalational, transdermal, transmucosal, and rectal administration.

For oral administration, suitable pharmaceutical compositions of PDE10 inhibitors include powders, granules, pills, tablets, and capsules as well as liquids, syrups, suspensions, and emulsions. These compositions may also include flavorants, preservatives, suspending, thickening and emulsifying agents, and other pharmaceutically acceptable additives and excipients. For parenteral administration, the compounds of the present invention can be prepared in aqueous injection solutions which may contain, in addition to the PDE10 inhibitor, buffers, antioxidants, bacteriostats, and other additives and excipients commonly employed in such solutions. Compositions of the present invention may be carried in a delivery system to provide for sustained release or enhanced uptake or activity of the therapeutic compound, such as a liposomal or hydrogel system for injection, a microparticle, nanopartical or micelle system for oral or parenteral delivery, or a staged capsule system for oral delivery.

In a further advantage of the present invention, compounds of structures (I) through (VI) are expected to avoid or reduce metabolic side effects associated with conventional antipsychotics, in particular the incidence of therapeutically induced obesity. For example, chronic use of olanzapine (Zyprexa®), the most widely prescribed medication to treat schizophrenia, and related atypical antipsychotics is associated with significant metabolic side effects including obesity and associated conditions such as diabetes.

In animals, subchronic treatment with olanzapine stimulates food intake and increases body weight, consistent with human situations. Furthermore, olanzapine acutely lowers blood leptin levels. Leptin is a satiety hormone produced from adipose tissues, and decrease of leptin level stimulates appetite. It is theorized that olanzapine could stimulate food intake at least partly by reducing leptin levels. Acute administration of olanzapine also changes the animal's response in glucose and insulin levels in glucose tolerance tests, which may also be directly linked to olanzapine's effect in food intake and body weight gain. Examination of the acute effect of PDE10 inhibitors of the present invention on metabolism, such as leptin, insulin and glucose changes during a metabolic challenge in standard animal models, as well as the chronic effect of PDE10 inhibitors of the present invention in food intake, body weight and energy homeostasis, in comparison with olanzapine should provide evidence to the pharmaceutical advantage of PDE10 inhibitors as antipsychotics in terms of less side-effect concerns.

The compositions of the present invention may be administered in combination with one or more additional therapeutic agents, in combination or by concurrent or sequential administration. Suitable additional agents (i.e., adjuvants) may include typical antipsychotics that block dopamine-$D_2$ receptors and serotonin $5HT_2$ receptors, e.g., haloperidol, fluphenazine, chlorpromazine, and atypical antipsychotics, e.g., clozapine, olanzapine, risperidone, quetiapine, ziprasidone.

Compounds of this invention may be assayed to determine their $IC_{50}$ values by a modification of the two-step method of Thompson and Appleman (Biochemistry 10; 311-316; 1971). In short, cAMP is spiked with ($^3$H)cAMP and incubated with PDE10 and various concentrations of a compound of structure (I). After the appropriate incubation time, the reaction is terminated by heating. The mixture is then subjected to treatment with snake venom phosphatase. The phosphatase hydrolyzes any AMP in the mixture, but leaves unreacted cAMP intact. Thus, by separating cAMP from the mixture and determining its concentration (by radiography), the percent of inhibition can be determined. $IC_{50}$ values can be calculated by performing the experiment at several concentrations using standard graphical means. A detailed description of the actual technique used for $IC_{50}$ assays are shown in Example 8. To this end, PDE10 inhibitors of the invention have an $IC_{50}$ of 100 μM or less, generally less than 10 μM, and typically less than 1 μM.

The following examples are provided for purposes of illustration, not limitation.

EXAMPLES

Example 1

(E)-2-(3-OXO-3,4-DIHYDRO-2H-BENZO[B][1,4]THIAZIN-2-YL)-N'-(3,4,5-TRIMETHOXYBENZYLIDENE)ACETOHYDRAZIDE

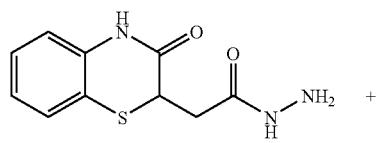

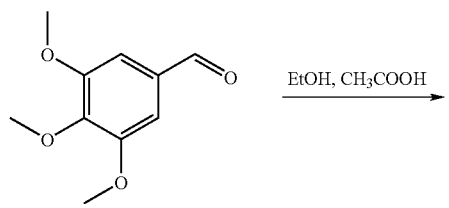

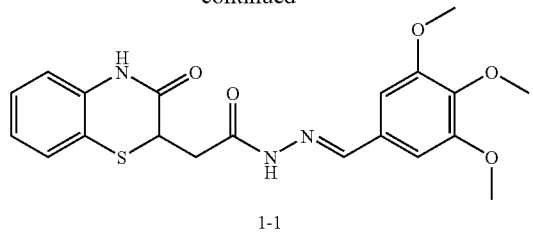

In a round-bottom glass flask equipped with a magnetic stir bar (3-Oxo-3,4-dihydro-2H-benzo[1,4]thiazin-2-yl)-acetic acid hydrazide (1 eq. 0.063 mmol; 15 mg) was dissolved in ethanol (3 mL) at room temperature. To this well stirred solution, acetic acid (~3 drops) and 3,4,5-trimethoxy-benzaldehyde solution (0.063 mmol; 12.4 mg dissolved in 0.5 mL of ethanol) were added, and the reaction mixture was stirred for another 5 hours at ambient temperature and monitored by TLC (typically with 1,2-dichloroethane-ethanol 5:1). The mixture was then concentrated under vacuum using a rotary evaporator. The crude product was diluted with hexanes and triturated. The precipitated solid product was transferred to a glass fiber funnel, the supernatant was removed by vacuum filtration and the solid was washed thoroughly with n-hexane twice to yield: 16 mg (61%) of 1-1.

Example 2

(E)-2-(1H-INDOL-3-YL)-N'-(3,4,5-TRIMETHOXY-BENZYLIDENE)ACETOHYDRAZIDE

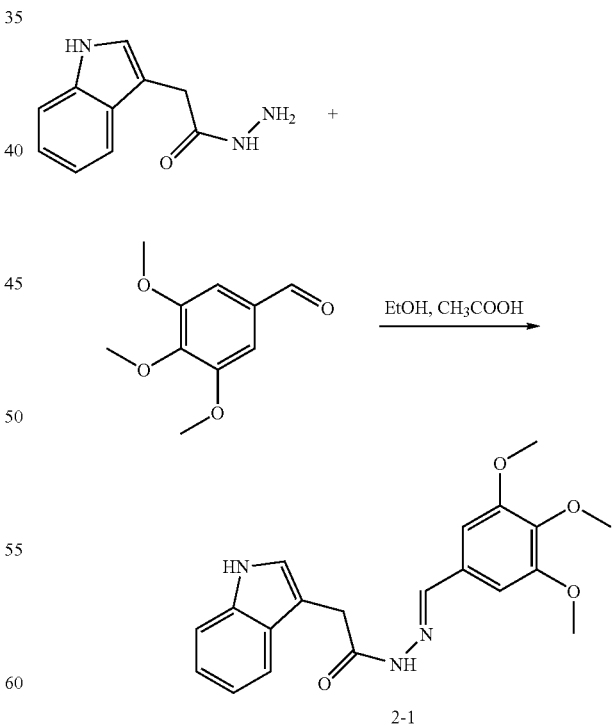

In a round-bottom glass flask equipped with a magnetic stir bar (1H-indol-3-yl)-acetic acid hydrazide (1 eq. 0.793 mmol; 150 mg) was dissolved in ethanol (10 mL) at room temperature. To this well stirred solution, acetic acid (~3 mL) and the 3,4,5-trimethoxy-benzaldehyde solution (1 eq. 0.793 mmol; 155.5 mg dissolved in 5 mL of ethanol) were added dropwise. The reaction mixture was stirred at room temperature until the reaction was complete (approximately 2 hours) as determined by TLC (typically with 1,2-dichloroethane-ethanol 5:1). The mixture was then concentrated under reduced pressure. The crude product was diluted with hexanes and triturated. The precipitated solid product was transferred to a glass fiber funnel, the supernatant was removed by vacuum filtration and the solid was washed thoroughly with n-hexane twice to yield 104 mg (36%) of 2-1.

Referring to Table 1 below, the listed derivatives of structure (II), where $R^3$, $R^4$ and $R^5$ are hydrogen, were synthesized according to the procedures outlined in Examples 1 and 2.

TABLE 1

(II)

| No. | MW | A | $R^1$ | x | $R^2$ |
|---|---|---|---|---|---|
| 1-1 | 415.47 | benzothiazinone | H | 3 | 3-$CH_3$<br>4-$CH_3$<br>5-$CH_3$ |
| 2-1 | 367.40 | indole | H | 3 | 3-$CH_3$<br>4-$CH_3$<br>5-$CH_3$ |
| 2-2 | 403.38 | indole | H | 3 | 3-$CH_3$<br>4-$CHF_2$<br>5-$CH_3$ |
| 2-3 | 367.40 | indole | H | 3 | 2-$CH_3$<br>4-$CH_3$<br>5-$CH_3$ |
| 2-4 | 415.47 | benzothiazinone | H | 3 | 2-$CH_3$<br>4-$CH_3$<br>5-$CH_3$ |
| 2-5 | 355.37 | indole | 2-F | 2 | 4-$CH_3$<br>5-$CH_3$ |

TABLE 1-continued (II)

| No. | MW | A | R¹ | x | R² |
|---|---|---|---|---|---|
| 2-6 | 410.43 | (1H-indol-3-yl) | H | 3 | 3-CH$_3$<br>4-CH$_2$CONH$_2$<br>5-CH$_3$ |
| 2-7 | 451.45 | (3-oxo-3,4-dihydro-2H-1,4-benzothiazin-2-yl) | H | 3 | 3-CH$_3$<br>4-CHF$_2$<br>5-CH$_3$ |
| 2-8 | 458.49 | (3-oxo-3,4-dihydro-2H-1,4-benzothiazin-2-yl) | H | 3 | 3-CH$_3$<br>4-CH$_2$CONH$_2$<br>5-CH$_3$ |
| 2-9 | 351.41 | (2-methyl-1H-indol-1-yl) | H | 2 | 3-CH$_3$<br>4-CH$_3$ |
| 2-10 | 338.37 | (1H-benzimidazol-1-yl) | H | 2 | 3-CH$_3$<br>4-CH$_3$ |
| 2-11 | 332.38 | (thiophen-2-yl) | H | 2 | 3-CH$_3$<br>2-COCH$_3$ |
| 2-12 | 339.35 | (1H-benzotriazol-1-yl) | H | 2 | 3-CH$_3$<br>4-CH$_3$ |
| 2-13 | 333.43 | (piperidin-1-yl) | H | 2 | 3-CH$_2$CH$_3$<br>4-CH$_2$CH$_3$ |

TABLE 1-continued (II)

| No. | MW | A | R¹ | x | R² |
|---|---|---|---|---|---|
| 2-14 | 488.54 | (1-substituted benzimidazol-2-ylmethyl)-3,4-dimethoxyphenyl group | H | 2 | 3-CH₃<br>4-CH₃ |
| 2-15 | 369.40 | 2-substituted-3-oxo-3,4-dihydro-2H-1,4-benzothiazine | H | 2 | 3-CH₂-4 |
| 2-16 | 371.41 | 2-substituted-3-oxo-3,4-dihydro-2H-1,4-benzothiazine | H | 2 | 3-H<br>4-CH₃ |
| 2-17 | 385.44 | 2-substituted-3-oxo-3,4-dihydro-2H-1,4-benzothiazine | H | 2 | 3-CH₂CH₃<br>4-H |
| 2-18 | 489.57 | 3-substituted-1H-indole | H | 2 | 3-benzyl<br>4-benzyl |

TABLE 1-continued (II)

| No. | MW | A | R¹ | x | R² |
|---|---|---|---|---|---|
| 2-19 | 321.34 | indol-3-yl | H | 2 | 3-CH₂-4 |
| 2-20 | 367.40 | indol-3-yl | H | 3 | 2-CH₃<br>3-CH₃<br>4-CH₃ |
| 2-21 | 491.57 | 3-oxo-3,4-dihydro-2H-benzo[b][1,4]thiazin-2-yl | H | 3 | 3-CH₃<br>4-benzyl<br>5-CH₃ |
| 2-22 | 443.50 | indol-3-yl | H | 3 | 3-CH₃<br>4-benzyl<br>5-CH₃ |
| 2-23 | 415.47 | 3-oxo-3,4-dihydro-2H-benzo[b][1,4]thiazin-2-yl | H | 3 | 2-CH₃<br>3-CH₃<br>4-CH₃ |
| 2-24 | 537.64 | 3-oxo-3,4-dihydro-2H-benzo[b][1,4]thiazin-2-yl | H | 2 | 3-benzyl<br>4-benzyl |

As used in Table 1 above, as well as in the tables that follow, the numbers preceding (and following in the case of alkanediyls) the $R^1$ and $R^2$ substituents refer to the substituent's position on the aromatic ring as shown below.

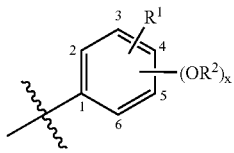

Example 3

(E)-N-(2-(2-(4-HYDROXY-3-METHOXYBENZYLIDENE)HYDRAZINYL)-2-OXOETHYL) ISONICOTINAMIDE

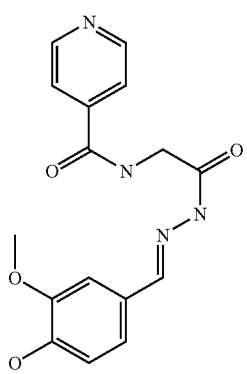

(3-1)

Referring to Table 2, the above derivative of structure (III), where $R^1$, $R^3$, $R^4$ and $R^5$ are hydrogen, can be synthesized by Reaction Scheme 2 from corresponding intermediate 5.

TABLE 2

(III)

| No. | MW | A | B | R | $R^6$ | x | $R^2$ |
|---|---|---|---|---|---|---|---|
| 3-1 | 328.32 | ![pyridyl] | $NR^6$ | =O | H | 2 | 3-$CH_3$ 4-H |

Example 4

(E)-2-(1-BENZYL-1H-BENZO[D]IMIDAZOL-2-YLTHIO)—N'-(4-ETHOXY-3-METHOXYBENZYLIDENE)ACETOHYDRAZIDE

Step 4A

Preparation of ethyl 2-(1H-benzo[d]imidazol-2-ylthio)acetate 4a

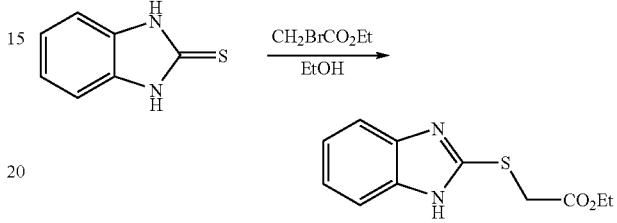

To a stirred solution of 1H-benzo[d]imidazole-2(3H)-thione (20.0 g, 0.13 mol, 1.0 eq.) in anhydrous ethanol (500 mL) at room temperature, was added potassium carbonate (9.25 g, 0.07 mol, 0.5 eq.) and ethyl bromoacetate (26.7 g, 0.16 mmol, 1.2 eq.). The reaction was heated to reflux and stirred at that temperature for 6 hours. The solvent was removed in vacuo and water (200 mL) was added. The aqueous phase was extracted with dichloromethane (3×100 mL), and the combined organic extracts were washed with water (200 mL) and brine (200 mL). The organic phase was dried over magnesium sulfate and concentrated in vacuo to give a colorless oil which solidified on standing. Purification by flash chromatography (CHCl$_3$→10% MeOH:90% CHCl$_3$) gave 4a as a white solid (11.7 g, 37%).

Step 4B

Preparation of ethyl 2-(1-benzyl-1H-benzo[d]imidazol-2-ylthio)acetate 4b

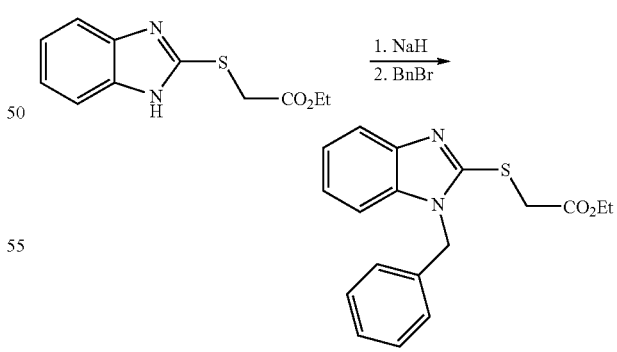

To a stirred solution of ethyl 2-(1H-benzo[d]imidazol-2-ylthio)acetate 4a (11.2 g, 47.6 mmol, 1.0 eq.) in 10:1 diethyl ether:dimethylformamide (450 mL) at 0° C., was added 60% sodium hydride in mineral oil (2.09 g, 52.3 mmol, 1.1 eq.), and the reaction was stirred at 0° C. for 20 minutes. Benzyl bromide (9.78 g, 57.1 mmol, 1.2 eq.) was added at 0° C., and the reaction was stirred with warming to room temperature for 16 hours. The reaction mixture was quenched with methanol (100 mL) and concentrated in vacuo. The residue was taken into hot chloroform (400 mL) and filtered. The filtrate was washed with water (200 mL), 1M HCl (200 mL) and brine (200 mL). The organic layer was dried over magnesium sulfate and concentrated in vacuo. Purification by flash chromatography (10% EtOAc:90% petroleum ether) gave 4b as a pale-yellow solid (4.82 g, 30%).

Step 4C

Preparation of 2-(1-benzyl-1H-benzo[d]imidazol-2-ylthio)acetohydrazide 4c

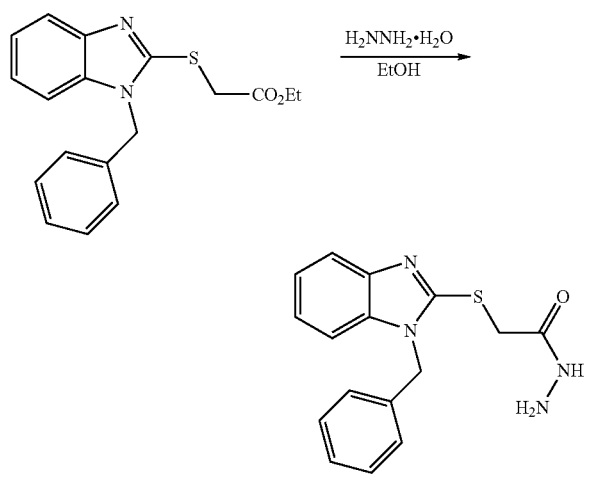

To a stirred solution of ethyl 2-(1-benzyl-1H-benzo[d]imidazol-2-ylthio)acetate 4b (200 mg, 0.61 mmol, 1.0 eq.) in ethanol (5 mL), was added hydrazine monohydrate (61 mg, 1.23 mmol, 2.0 eq.), and the reaction mixture was heated to reflux and stirred at that temperature for 16 hours. The reaction mixture was cooled to room temperature and concentrated in vacuo. The mixture was dissolved in ethyl acetate (20 mL) and washed with water (20 mL) and brine (20 mL). The organic layer was dried over magnesium sulfate and concentrated in vacuo giving 4c as a pale yellow solid which was used without further purification (200 mg, 100%).

Step 4D Preparation of (E)-2-(1-benzyl-1H-benzo[d]imidazol-2-ylthio)-N'-(4-ethoxy-3-methoxybenzylidene)acetohydrazide 4-1

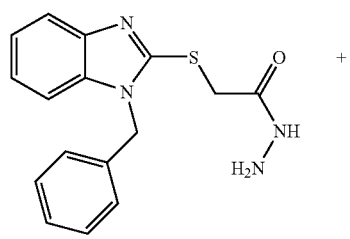

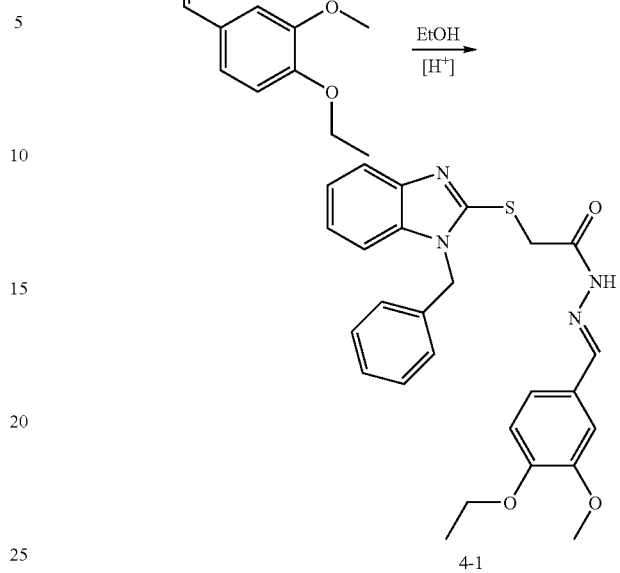

To a stirred solution of 2-(1-benzyl-1H-benzo[d]imidazol-2-ylthio)acetohydrazide 4c (200 mg, 0.61 mmol, 1.0 eq.) in ethanol (5 mL), was added 3-methoxy-4-ethoxybenzaldehyde (110 mg, 0.61 mmol, 1.0 eq.) and acetic acid (3 drops). The mixture was heated to reflux and stirred at that temperature for 16 hours. The reaction mixture was cooled to room temperature, and the precipitate that formed on cooling was filtered and washed with water (10 mL), ethanol (10 mL) and diethyl ether (10 mL). The solid was dried by high vacuum overnight giving 4-1 as a white solid (196 mg, 67%).

Example 5

(E)-N'-(3,4-DIMETHOXYBENZYLIDENE)-2-(2-METHYLQUINOLIN-4-YLTHIO)ACETOHYDRAZIDE HYDROCHLORIDE

Step 5A Preparation of 2-methylquinoline-4-thiol 5a

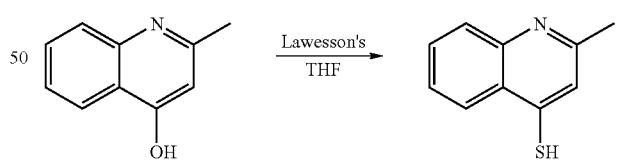

A stirred suspension of 2-methylquinolin-4-ol (5.10 g, 32.0 mmol, 1.0 eq.) in tetrahydrofuran (51 mL) was heated to 50° C., and 6.5 g of Lawesson's Reagent (6.5 g, 16.0 mmol, 0.5 eq.) was added in one portion. The reaction was heated to 80° C. and stirred at that temperature for 6 hours. The reaction was poured into a hot biphasic solution of ethyl acetate (200 mL) and water (200 mL) and was vigorously stirred. A viscous orange gel precipitated from the solution. The water/ethyl acetate solution was decanted into a separating funnel and the organic layer isolated. The aqueous layer was extracted with ethyl acetate (4×200 ml), and the combined extracts were dried over magnesium sulfate. The solution was filtered and concentrated in vacuo. The resulting orange gel was purified by flash chromatography (50% EtOAc:50% petroleum ether→100% EtOAc) to yield 5a as a yellow solid (1.70 g, 30%).

Step 5B Preparation of methyl 2-(2-methylquinolin-4-ylthio)acetate 5b

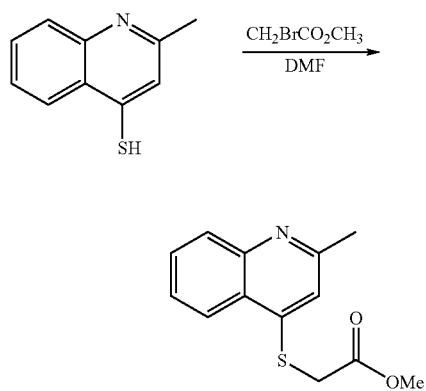

2-methylquinoline-4-thiol 5a (1.00 g, 5.71 mmol, 1.00 eq.) was dissolved in dimethylformamide (10 mL) at room temperature. Potassium carbonate (0.87 g, 6.28 mmol, 1.10 eq.) was added and the mixture was stirred for 15 minutes. Methyl bromoacetate (921 mg, 6.02 mmol, 1.05 eq.) was added dropwise to the solution, and the reaction was stirred at room temperature for 2.5 hours. Water (20 mL) was added to the reaction mixture, and the aqueous layer was extracted with ethyl acetate (30 mL). The aqueous layer was further extracted with ethyl acetate (3×50 mL), and the combined organic layers were dried over magnesium sulfate, filtered and concentrated in vacuo. The resulting residue was dried on high vacuum to yield 5b as a brown solid (1.25 g, 88%).

Step 5C Preparation of 2-(2-methylquinolin-4-ylthio)acetohydrazide 5c

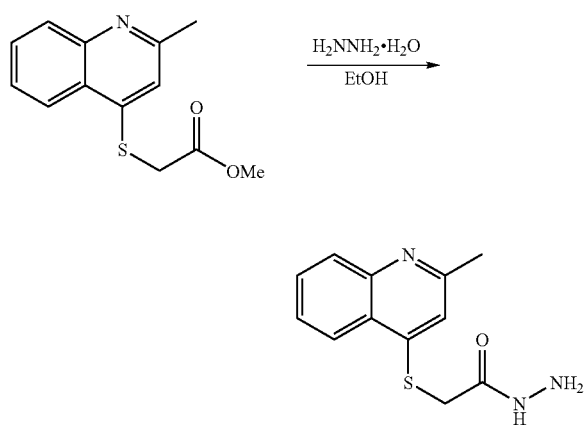

Example 5, Step 5C was performed in an analogous fashion to Example 4, Step 4C.

Step 5D Preparation of (E)-N'-(3,4-dimethoxybenzylidene)-2-(2-methylquinolin-4-ylthio)acetohydrazide 5-1

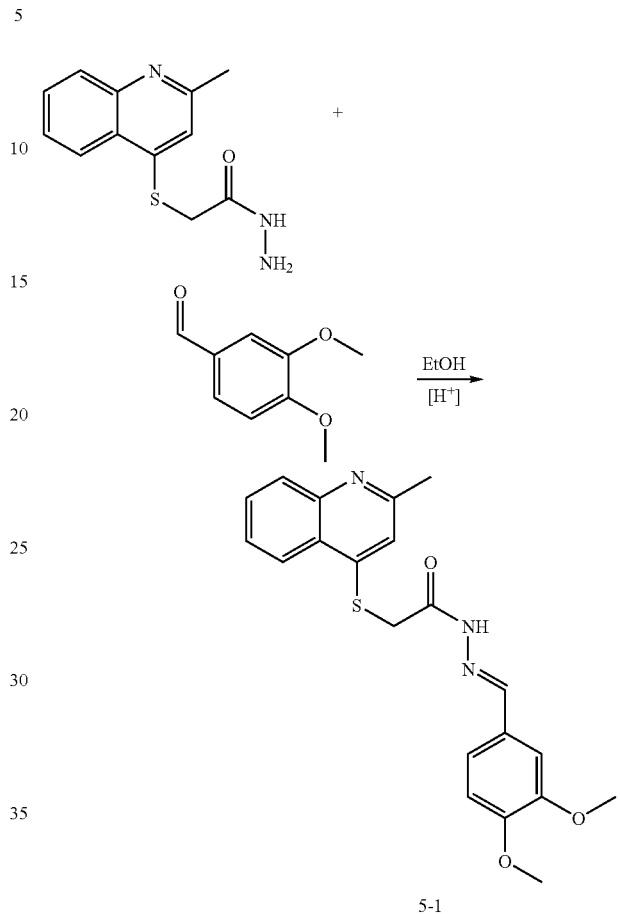

Example 5, Step 5D was performed in an analogous fashion to Example 4, Step 4D.

Step 5E Preparation of (E)-N'-(3,4-dimethoxybenzylidene)-2-(2-methylquinolin-4-ylthio)acetohydrazide hydrochloride 5-1a

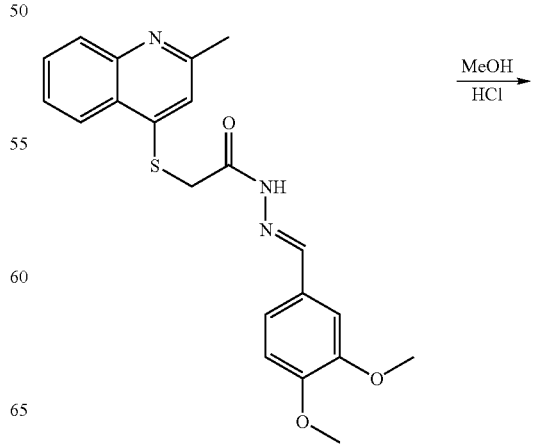

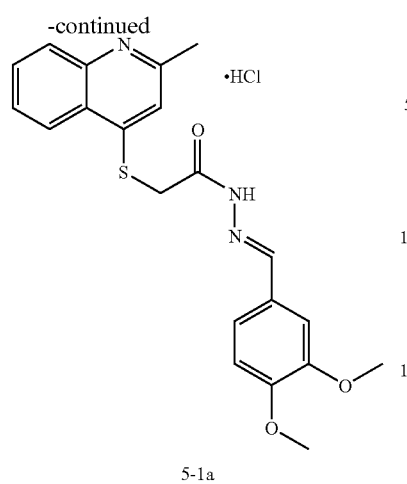

5-1a 2-(2-methylquinolin-4-ylsulfanyl)-acetic acid-(3,4-dimethoxybenzylidene)-hydrazide 5-1 (220 mg, 0.56 mmol, 1.0 eq.) in methanol (40 mL) and dimethylsulfoxide (2 mL) was heated to 100° C. for 2 hours until completely dissolved before being allowed to cool to 50° C. 1.25 M methanolic hydrochloric acid (1 eq.) was then added, and the mixture was stirred for 20 min before partially concentrating in vacuo. The product was then obtained through filtration and dried to give 5-1a (180 mg, 75%).

Referring to Table 3, the following derivatives of structure (IV), wherein $R^3$ is hydrogen, were synthesized according to the procedures outlined in Examples 4 and 5 (in the following table, an $R^1$ substituent is absent when H is designated).

TABLE 3

(IV)

| No. | MW | A | B | $R^1$ | p | x | $R^2$ | $R^4$ | $R^5$ |
|---|---|---|---|---|---|---|---|---|---|
| 4-1 | 474.58 | 1-benzyl-benzimidazol-2-yl | S | H | 1 | 2 | 3-CH$_3$<br>4-CH$_2$CH$_3$ | H | H |
| 5-1 | 395.48 | 2-methylquinolin-4-yl | S | H | 1 | 2 | 3-CH$_3$<br>4-CH$_3$ | H | H |
| 5-2 | 526.56 | 1-benzyl-benzimidazol-2-yl | S | H | 1 | 3 | 3-CH$_3$<br>4-CHF$_2$<br>5-CH$_3$ | H | H |

TABLE 3-continued
(IV)
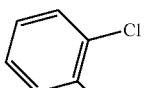
| No. | MW | A | B | R¹ | p | x | R² | R⁴ | R⁵ |
|---|---|---|---|---|---|---|---|---|---|
| 5-3 | 561.01 | 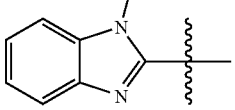 | S | H | 1 | 3 | 3-CH₃<br>4-CHF₂<br>5-CH₃ | H | H |
| 5-4 | 512.99 | 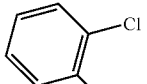 | S | 2-F | 1 | 2 | 4-CH₃<br>5-CH₃ | H | H |
| 5-5 | 525.03 | 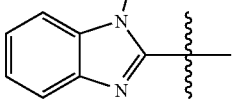 | S | H | 1 | 3 | 2-CH₃<br>4-CH₃<br>5-CH₃ | H | H |
| 5-6 | 525.03 | 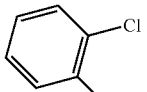 | S | H | 1 | 3 | 3-CH₂CH₃<br>4-H | H | H |
| 5-7 | 478.55 | 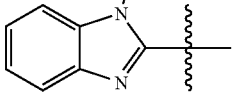 | S | 2-F | 1 | 2 | 4-CH₃<br>5-CH₃ | H | H |

TABLE 3-continued
(IV)
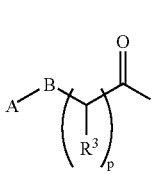
| No. | MW | A | B | R¹ | p | x | R² | R⁴ | R⁵ |
|---|---|---|---|---|---|---|---|---|---|
| 5-8 | 460.56 | 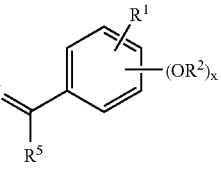 | S | H | 1 | 2 | 3-CH$_2$CH$_3$<br>4-H | H | H |
| 5-9 | 490.58 | 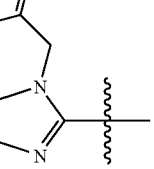 | S | H | 1 | 3 | 2-CH$_3$<br>4-CH$_3$<br>5-CH$_3$ | H | H |
| 5-10 | 533.61 |  | S | H | 1 | 3 | 3-CH$_3$<br>4-CH$_2$CONH$_2$<br>5-CH$_3$ | H | H |
| 5-11 | 460.56 | 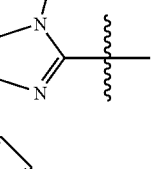 | S | H | 1 | 2 | 2-CH$_3$<br>4-CH$_3$ | H | H |
| 5-12 | 411.48 | 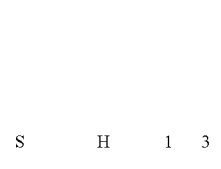 | S | H | 1 | 2 | 3-CH$_3$<br>4-CH$_3$ | H | H |
| 5-13 | 360.44 | 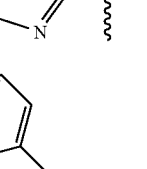 | S | H | 1 | 2 | 3-CH$_3$<br>4-CH$_3$ | H | H |

TABLE 3-continued
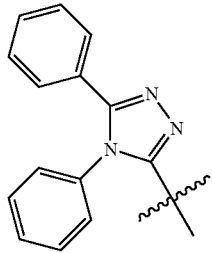
(IV)
| No. | MW | A | B | R¹ | p | x | R² | R⁴ | R⁵ |
|---|---|---|---|---|---|---|---|---|---|
| 5-14 | 473.55 | 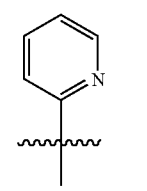 | S | H | 1 | 2 | 3-CH₃<br>4-CH₃ | H | H |
| 5-15 | 331.39 | 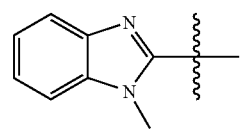 | S | H | 1 | 2 | 3-CH₃<br>4-CH₃ | H | H |
| 5-16 | 384.46 | 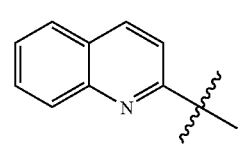 | S | H | 1 | 2 | 3-CH₃<br>4-CH₃ | H | H |
| 5-17 | 381.45 | 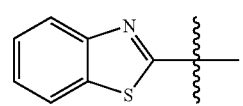 | S | H | 1 | 2 | 3-CH₃<br>4-CH₃ | H | H |
| 5-18 | 387.48 | 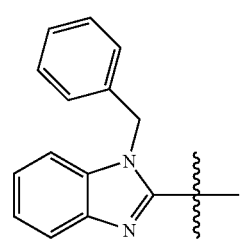 | S | H | 1 | 2 | 2-CH₃<br>3-CH₃ | H | H |
| 5-19 | 430.53 | 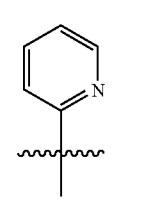 | S | H | 1 | 1 | 4-CH₃ | H | H |
| 5-20 | 331.39 |  | S | H | 1 | 2 | 3-H<br>4-CH₂CH₃ | H | H |

TABLE 3-continued
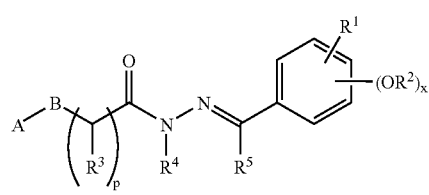
(IV)
| No. | MW | A | B | R¹ | p | x | R² | R⁴ | R⁵ |
|---|---|---|---|---|---|---|---|---|---|
| 5-21 | 361.42 | 2-pyridyl | S | H | 1 | 3 | 3-$CH_3$<br>4-$CH_3$<br>5-$CH_3$ | H | H |
| 5-22 | 459.53 | 4,5-diphenyl-4H-1,2,4-triazol-3-yl | S | H | 1 | 2 | 3-$CH_3$<br>4-H | H | H |
| 5-23 | 432.50 | 1-benzyl-1H-benzimidazol-2-yl | S | H | 1 | 2 | 3-H<br>4-H | H | H |
| 5-24 | 370.43 | 1H-benzimidazol-2-yl | S | H | 1 | 2 | 3-$CH_3$<br>4-$CH_3$ | H | H |
| 5-25 | 490.58 | 1-benzyl-1H-benzimidazol-2-yl | S | H | 1 | 3 | 3-$CH_3$<br>4-$CH_3$<br>5-$CH_3$ | H | H |
| 5-26 | 460.56 | 1-benzyl-1H-benzimidazol-2-yl | S | H | 1 | 2 | 3-$CH_3$<br>4-$CH_3$ | H | H |

TABLE 3-continued
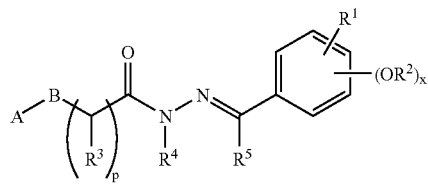
(IV)
| No. | MW | A | B | R¹ | p | x | R² | R⁴ | R⁵ |
|---|---|---|---|---|---|---|---|---|---|
| 5-27 | 495.00 | 2-Cl-benzyl-benzimidazolyl | S | H | 1 | 2 | 3-CH₃, 4-CH₃ | H | H |
| 5-28 | 474.54 | 3-phenyl-4(3H)-quinazolinon-2-yl | S | H | 1 | 2 | 3-CH₃, 4-CH₃ | H | H |
| 5-29 | 409.51 | 4,8-dimethylquinolin-2-yl | S | H | 1 | 2 | 3-CH₃, 4-CH₃ | H | H |
| 5-30 | 387.48 | benzothiazol-2-yl | S | H | 1 | 2 | 3-CH₃, 4-CH₃ | H | H |
| 5-31 | 474.58 | 4-methylbenzyl-benzimidazolyl | S | H | 1 | 2 | 3-CH₃, 4-CH₃ | H | H |
| 5-32 | 371.41 | benzoxazol-2-yl | S | H | 1 | 2 | 3-CH₃, 4-CH₃ | H | H |

TABLE 3-continued
(IV)
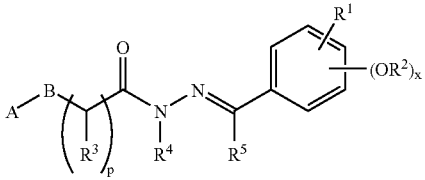
| No. | MW | A | B | R¹ | p | x | R² | R⁴ | R⁵ |
|---|---|---|---|---|---|---|---|---|---|
| 5-33 | 495.00 | 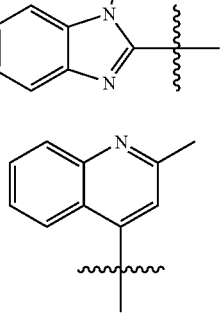 | S | H | 1 | 2 | 3-CH₃<br>4-CH₃ | H | H |
| 5-34 | 423.47 | 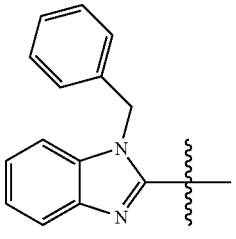 | O | H | 1 | 3 | 3-CH₃<br>4-CH₂CH₃<br>5-CH₃ | H | H |
| 5-35 | 446.53 | 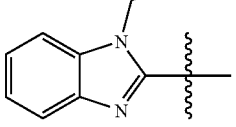 | S | H | 1 | 2 | 3-CH₃<br>4-H | H | H |
| 5-35 | 398.48 | 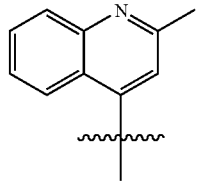 | S | H | 1 | 2 | 3-CH₃<br>4-CH₃ | H | H |
| 5-37 | 379.42 | 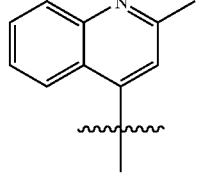 | O | H | 1 | 2 | 3-CH₃<br>4-CH₃ | H | H |
| 5-38 | 433.51 | 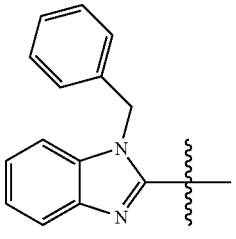 | O | H | 1 | 2 | 3-CH₃<br>4-cyclopentyl | H | H |

TABLE 3-continued
(IV)
| No. | MW | A | B | R¹ | p | x | R² | R⁴ | R⁵ |
|---|---|---|---|---|---|---|---|---|---|
| 5-39 | 504.61 | 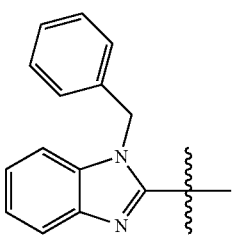 | S | H | 1 | 3 | 3-$CH_3$<br>4-$CH_2CH_3$<br>5-$CH_3$ | H | H |
| 5-40 | 488.61 | 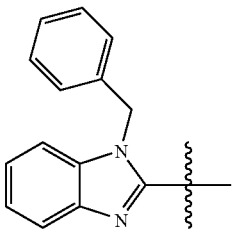 | S | H | 1 | 2 | 3-$CH_3$<br>4-n-propyl | H | H |
| 5-41 | 488.61 | 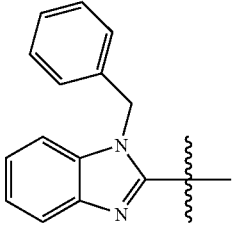 | S | H | 1 | 2 | 3-$CH_3CH_3$<br>4-$CH_2CH_3$ | H | H |
| 5-42 | 463.53 | 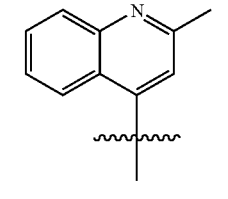 | O | H | 1 | 3 | 3-$CH_3$<br>4-cyclopentyl<br>5-$CH_3$ | H | H |
| 5-43 | 486.59 | 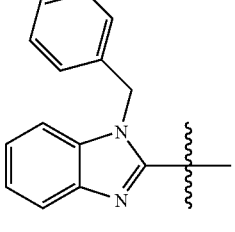 | S | H | 1 | 2 | 3-$CH_3$<br>4-(2)-propenyl | H | H |

TABLE 3-continued
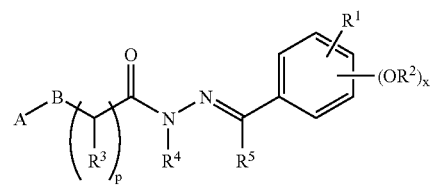
(IV)
| No. | MW | A | B | R¹ | p | x | R² | R⁴ | R⁵ |
|---|---|---|---|---|---|---|---|---|---|
| 5-44 | 474.58 | 1-benzyl-benzimidazol-2-yl | S | H | 1 | 2 | 3-$CH_3$, 4-$CH_2CH_3$ | H | H |
| 5-45 | 423.53 | 2-methylquinolin-4-yl | S | H | 1 | 2 | 3-$CH_3$, 4-n-propyl | H | H |
| 5-46 | 407.47 | 2-methylquinolin-4-yl | O | H | 1 | 2 | 3-$CH_3$, 4-n-propyl | H | H |
| 5-47 | 514.65 | 1-benzyl-benzimidazol-2-yl | S | H | 1 | 2 | 3-cyclopentyl, 4-$CH_3$ | H | H |
| 5-48 | 444.51 | 1-benzyl-benzimidazol-2-yl | S | H | 1 | 2 | 3-$CH_2$-4 | H | H |
| 5-49 | 514.65 | 1-benzyl-benzimidazol-2-yl | S | H | 1 | 2 | 3-$CH_3$, 4-cyclopentyl | H | H |

TABLE 3-continued (IV)

| No. | MW | A | B | R¹ | p | x | R² | R⁴ | R⁵ |
|---|---|---|---|---|---|---|---|---|---|
| 5-50 | 518.64 | 1-benzyl-benzimidazol-2-yl | S | H | 1 | 3 | 3-CH₃<br>4-n-propyl<br>5-CH₃ | H | H |
| 5-51 | 544.67 | 1-benzyl-benzimidazol-2-yl | S | H | 1 | 3 | 3-CH₃<br>4-cyclopentyl<br>5-CH₃ | H | H |
| 5-52 | 612.75 | 1-benzyl-benzimidazol-2-yl | S | H | 1 | 2 | 3-benzyl<br>4-benzyl | H | H |
| 5-53 | 446.53 | 1-benzyl-benzimidazol-2-yl | S | H | 1 | 2 | 3-H<br>4-CH₃ | H | H |
| 5-54 | 490.58 | 1-benzyl-benzimidazol-2-yl | S | H | 1 | 3 | 2-CH₃<br>3-CH₃<br>4-CH₃ | H | H |

TABLE 3-continued
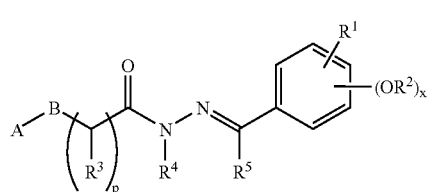
(IV)
| No. | MW | A | B | R$^1$ | p | x | R$^2$ | R$^4$ | R$^5$ |
|---|---|---|---|---|---|---|---|---|---|
| 5-55 | 566.68 | 1-benzyl-benzimidazol-2-yl | S | H | 1 | 3 | 3-CH$_3$<br>4-benzyl<br>5-CH$_3$ | H | H |
| 5-56 | 647.20 | 1-(2-chlorobenzyl)-benzimidazol-2-yl | S | H | 1 | 2 | 3-benzyl<br>4-benzyl | H | H |
| 5-57 | 478.96 | 1-(2-chlorobenzyl)-benzimidazol-2-yl | S | H | 1 | 2 | 3-CH$_2$-4 | H | H |
| 5-58 | 480.97 | 1-(2-chlorobenzyl)-benzimidazol-2-yl | S | H | 1 | 2 | 3-H<br>4-CH$_3$ | H | H |
| 5-59 | 525.03 | 1-(2-chlorobenzyl)-benzimidazol-2-yl | S | H | 1 | 3 | 2-CH$_3$<br>3-CH$_3$<br>4-CH$_3$ | H | H |

TABLE 3-continued
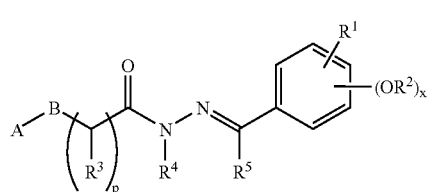
(IV)
| No. | MW | A | B | R¹ | p | x | R² | R⁴ | R⁵ |
|---|---|---|---|---|---|---|---|---|---|
| 5-60 | 601.12 | 1-(2-chlorobenzyl)benzimidazol-2-yl | S | H | 1 | 3 | 3-$CH_3$<br>4-benzyl<br>5-$CH_3$ | H | H |
| 5-61 | 456.55 | 1-benzylbenzimidazol-2-yl | $CH_2$ | H | 1 | 2 | 3-n-propyl<br>4-$CH_3$ | H | H |
| 5-62 | 486.59 | 1-benzylbenzimidazol-2-yl | $CH_2$ | H | 1 | 2 | 3-$CH_2CH_3$<br>4-$CH_3$ | H | H |
| 5-63 | 460.56 | 1-benzylbenzimidazol-2-yl | S | H | 1 | 2 | 3-$CH_3$<br>5-$CH_3$ | H | H |
| 5-64 | 476.55 | 1-benzylbenzimidazol-2-yl | S | H | 1 | 3 | 3-$CH_3$<br>4-H<br>5-$CH_3$ | H | H |

TABLE 3-continued
(IV)
| No. | MW | A | B | R¹ | p | x | R² | R⁴ | R⁵ |
|---|---|---|---|---|---|---|---|---|---|
| 5-65 | 486.59 | 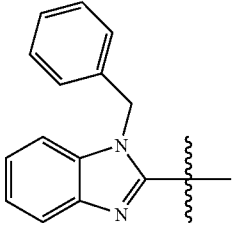 | S | H | 1 | 2 | 3-cyclopropyl 4-CH₃ | H | H |
| 5-66 | 464.97 | 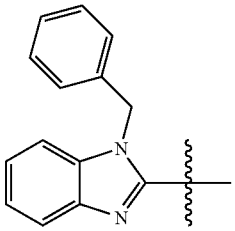 | S | 3-Cl | 1 | 1 | 4-CH₃ | H | H |
| 5-67 | 474.58 | 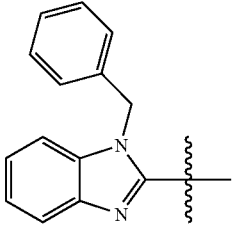 | S | H | 1 | 2 | 3-CH₂CH₃ 4-CH₃ | H | H |
| 5-68 | 446.53 | 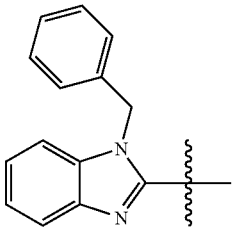 | S | H | 1 | 2 | 3-H 4-CH₃ | H | H |
| 5-69 | 409.51 | 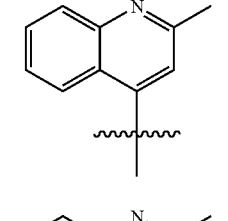 | S | H | 1 | 2 | 3-CH₃ 4-CH₃ | H | CH₃ |
| 5-70 | 365.45 | 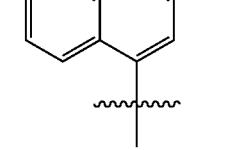 | S | H | 1 | 1 | 4-CH₃ | H | H |

TABLE 3-continued
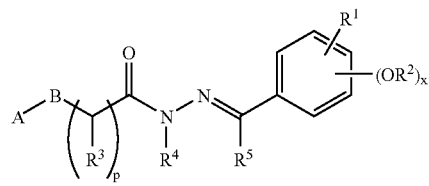
(IV)
| No. | MW | A | B | R¹ | p | x | R² | R⁴ | R⁵ |
|---|---|---|---|---|---|---|---|---|---|
| 5-71 | 474.38 | 2-methylquinolin-4-yl | S | 3-Br | 1 | 2 | 4-H<br>5-$CH_2CH_3$ | H | H |
| 5-72 | 349.39 | 2-methylquinolin-4-yl | O | H | 1 | 1 | 2-$CH_3$ | H | H |
| 5-73 | 395.48 | 2-methylquinolin-4-yl | S | 5-$CH_3$ | 1 | 2 | 3-$CH_3$<br>4-H | H | H |
| 5-74 | 423.47 | 8-methoxy-2,5-dimethylquinolin-4-yl | O | H | 1 | 2 | 3-$CH_3$<br>4-$CH_3$ | H | H |
| 5-75 | 409.46 | 2-methylquinolin-4-yl | S | H | 1 | 3 | 3,4-$CH_2$-<br>5-$CH_3$ | H | H |
| 5-76 | 429.93 | 2-methylquinolin-4-yl | S | 3-Cl | 1 | 2 | 4-$CH_3$<br>5-$CH_3$ | H | H |

TABLE 3-continued (IV)

| No. | MW | A | B | R¹ | p | x | R² | R⁴ | R⁵ |
|---|---|---|---|---|---|---|---|---|---|
| 5-77 | 474.38 | 2-methylquinolin-4-yl | S | 3-Br | 1 | 2 | 4-CH₃ 5-CH₃ | H | H |
| 5-78 | 409.44 | 8-methoxy-2-methylquinolin-4-yl | O | H | 1 | 2 | 3-CH₃ 4-CH₃ | H | H |
| 5-79 | 415.46 | 2-methylquinolin-4-yl | S | 4-CHF₂ | 1 | 1 | 3-CH₃ | H | H |
| 5-80 | 365.39 | 2-methylquinolin-4-yl | O | H | 1 | 2 | 3-CH₃ 4-H | H | H |
| 5-81 | 363.42 | 2-methylquinolin-4-yl | O | 3-CH₃ | 1 | 1 | 4-CH₃ | H | H |
| 5-82 | 439.47 | 6,7-dimethoxy-2-methylquinolin-4-yl | O | H | 1 | 2 | 3-CH₃ 4-CH₃ | H | H |

TABLE 3-continued
(IV)
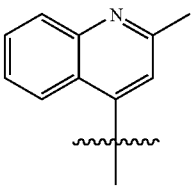
| No. | MW | A | B | R¹ | p | x | R² | R⁴ | R⁵ |
|---|---|---|---|---|---|---|---|---|---|
| 5-83 | 378.43 | 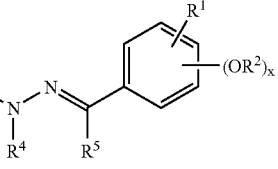 | NR⁶ (R⁶ = H) | H | 1 | 2 | 3-CH₃ 4-CH₃ | H | H |
| 5-84 | 365.39 | 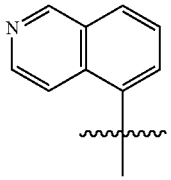 | O | H | 1 | 2 | 3-CH₃ 4-CH₃ | H | H |
| 5-85 | 444.29 | 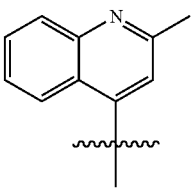 | O | 2-Br | 1 | 2 | 3-H 4-CH₃ | H | H |
| 5-86 | 393.40 | 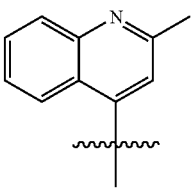 | O | H | 1 | 3 | 3-CH₂-4 5-CH₃ | H | H |
| 5-87 | 397.41 | 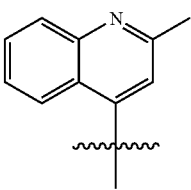 | O | 2-F | 1 | 2 | 4-CH₃ 5-CH₃ | H | H |
| 5-88 | 367.38 | 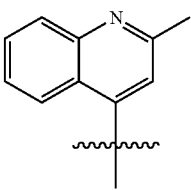 | O | 4-F | 1 | 1 | 3-CH₃ | H | H |

TABLE 3-continued (IV)

| No. | MW | A | B | R¹ | p | x | R² | R⁴ | R⁵ |
|---|---|---|---|---|---|---|---|---|---|
| 5-89 | 399.83 | 2-methylquinolin-4-yl | O | 3-Cl | 1 | 2 | 4-H 5-CH$_3$ | H | H |
| 5-90 | 458.32 | 2-methylquinolin-4-yl | O | 3-Br | 1 | 2 | 4-H 5-CH$_2$CH$_3$ | H | H |
| 5-91 | 413.86 | 2-methylquinolin-4-yl | O | 3-Cl | 1 | 2 | 4-CH$_3$ 5-CH$_3$ | H | H |
| 5-92 | 458.32 | 2-methylquinolin-4-yl | O | 3-Br | 1 | 2 | 4-CH$_3$ 5-CH$_3$ | H | H |
| 5-93 | 371.41 | thieno[3,2-b]pyridin-7-yl | O | H | 1 | 2 | 3-CH$_3$ 4-CH$_3$ | H | H |
| 5-94 | 383.38 | 2-methylquinolin-4-yl | O | 3-F | 1 | 2 | 4-H 5-CH$_3$ | H | H |

TABLE 3-continued (IV)

| No. | MW | A | B | R¹ | p | x | R² | R⁴ | R⁵ |
|---|---|---|---|---|---|---|---|---|---|
| 5-95 | 383.83 | 2-methylquinolin-4-yl | O | 3-Cl | 1 | 1 | 4-$CH_3$ | H | H |
| 5-96 | 429.42 | 2-methylquinolin-4-yl | O | H | 1 | 2 | 3-$CH_2CH_3$<br>4-$CHF_2$ | H | H |
| 5-97 | 415.40 | 2-methylquinolin-4-yl | O | H | 1 | 2 | 3-$CH_3$<br>4-$CHF_2$ | H | H |
| 5-98 | 379.42 | 2-methylquinolin-4-yl | O | 3-$CH_3$ | 1 | 2 | 4-H<br>5-$CH_3$ | H | H |
| 5-99 | 399.40 | 2-methylquinolin-4-yl | O | 4-$CHF_2$ | 1 | 1 | 3-$CH_3$ | H | H |
| 5-100 | 409.44 | 2-methylquinolin-4-yl | O | H | 1 | 3 | 2-$CH_3$<br>3-$CH_3$<br>4-$CH_3$ | H | H |

TABLE 3-continued
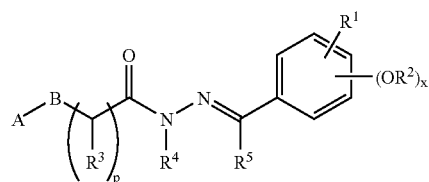
(IV)
| No. | MW | A | B | R¹ | p | x | R² | R⁴ | R⁵ |
|---|---|---|---|---|---|---|---|---|---|
| 5-101 | 409.44 | 4-(2-methylquinolinyl) | O | H | 1 | 3 | 2-$CH_3$<br>4-$CH_3$<br>5-$CH_3$ | H | H |
| 5-102 | 435.42 | 4-(2-methylquinolinyl) | S | H | 1 | 2 | 3-$CF_3$<br>4-H | H | H |
| 5-103 | 395.48 | 4-(2-methylquinolinyl) | S | H | 1 | 2 | 3-$CH_2CH_3$<br>4-H | H | H |
| 5-104 | 409.51 | 4-(2-methylquinolinyl) | S | H | 1 | 2 | 3-$CH_3$<br>4-$CH_2CH_3$ | H | H |
| 5-105 | 409.51 | 4-(2-methylquinolinyl) | S | H | 1 | 2 | 3-$CH_2CH_3$<br>4-$CH_3$ | H | H |
| 5-106 | 447.41 | 8-$CF_3$-2-methylquinolin-4-yl | O | H | 1 | 2 | 3-$CH_3$<br>4-$CH_3$ | H | H |

TABLE 3-continued (IV)

| No. | MW | A | B | R¹ | p | x | R² | R⁴ | R⁵ |
|---|---|---|---|---|---|---|---|---|---|
| 5-107 | 424.41 | 6-nitro-2-methylquinolin-4-yl | O | H | 1 | 2 | 3-CH$_3$<br>4-CH$_3$ | H | H |
| 5-108 | 365.45 | 2-methylquinolin-4-yl | S | H | 1 | 1 | 3-CH$_3$ | H | H |
| 5-109 | 395.48 | 2-methylquinolin-4-yl | S | H | 1 | 2 | 3-CH$_3$<br>5-CH$_3$ | H | H |
| 5-110 | 411.48 | 2-methylquinolin-4-yl | S | H | 1 | 3 | 3-CH$_3$<br>4-H<br>5-CH$_3$ | H | H |
| 5-111 | 431.46 | 2-methylquinolin-4-yl | S | H | 1 | 2 | 3-CHF$_2$<br>4-CH$_3$ | H | H |
| 5-112 | 437.56 | 2-methylquinolin-4-yl | S | H | 1 | 2 | 3-CH$_2$CH(CH$_3$)$_2$<br>4-CH$_3$ | H | H |

TABLE 3-continued (IV)

| No. | MW | A | B | R¹ | p | x | R² | R⁴ | R⁵ |
|---|---|---|---|---|---|---|---|---|---|
| 5-113 | 449.45 | 2-methylquinolin-4-yl | S | H | 1 | 2 | 3-CF₃<br>4-H | H | H |
| 5-114 | 425.51 | 6-methoxy-2-methylquinolin-4-yl | S | H | 1 | 2 | 3-CH₃<br>4-CH₃ | H | H |
| 5-115 | 486.59 | 1-benzyl-1H-benzimidazol-2-yl | S | H | 1 | 2 | 3-(2)-propenyl<br>4-CH₃ | H | H |
| 5-116 | 488.61 | 1-benzyl-1H-benzimidazol-2-yl | S | H | 1 | 2 | 3-n-propyl<br>4-CH₃ | H | H |
| 5-117 | 400.46 | 1H-benzimidazol-2-yl | S | H | 1 | 3 | 3-CH₃<br>4-CH₃<br>5-CH₃ | H | H |
| 5-118 | 454.50 | quinolin-4-yl | S | H | 1 | 3 | 3-CH₃<br>4-CH₂CONH₂<br>5-CH₃ | H | H |

TABLE 3-continued
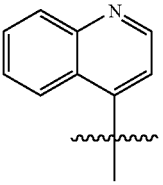
(IV)
| No. | MW | A | B | R¹ | p | x | R² | R⁴ | R⁵ |
|---|---|---|---|---|---|---|---|---|---|
| 5-119 | 447.46 | 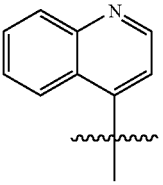 | S | H | 1 | 3 | 3-CH₃<br>4-CHF₂<br>5-CH₃ | H | H |
| 5-120 | 487.58 | 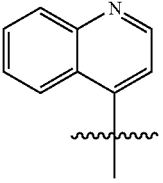 | S | H | 1 | 3 | 3-CH₃<br>4-benzyl<br>5-CH₃ | H | H |
| 5-121 | 399.44 | 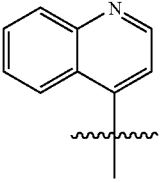 | S | 2-F | 1 | 2 | 4-CH₃<br>5-CH₃ | H | H |
| 5-122 | 411.48 | 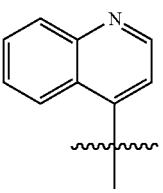 | S | H | 1 | 3 | 3-CH₃<br>4-CH₃<br>5-CH₃ | H | H |
| 5-123 | 411.48 | 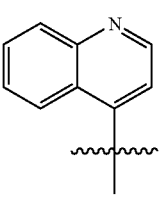 | S | H | 1 | 3 | 2-CH₃<br>4-CH₃<br>5-CH₃ | H | H |
| 5-124 | 411.48 | 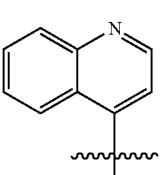 | S | H | 1 | 3 | 2-CH₃<br>3-CH₃<br>4-CH₃ | H | H |
Note: R² values shown use subscripts as $3\text{-}CH_3$, $4\text{-}CHF_2$, $5\text{-}CH_3$, etc.

TABLE 3-continued (IV)

| No. | MW | A | B | R¹ | p | x | R² | R⁴ | R⁵ |
|---|---|---|---|---|---|---|---|---|---|
| 5-125 | 381.45 | 4-quinolinyl | S | H | 1 | 2 | 3-CH$_2$CH$_3$<br>4-H | H | H |
| 5-126 | 367.43 | 4-quinolinyl | S | H | 1 | 2 | 3-H<br>4-CH$_3$ | H | H |
| 5-127 | 365.41 | 4-quinolinyl | S | H | 1 | 2 | 3-CH$_2$-4 | H | H |
| 5-128 | 533.65 | 4-quinolinyl | S | H | 1 | 2 | 3-benzyl<br>4-benzyl | H | H |
| 5-129 | 525.03 | 1-(2-chlorobenzyl)benzimidazol-2-yl | S | H | 1 | 3 | 3-CH$_3$<br>4-CH$_3$<br>5-CH$_3$ | H | H |
| 5-130 | 490.57 | 1-benzylbenzimidazol-2-yl | S | H | 1 | 3 | 3-CH$_3$<br>4-CH$_3$<br>5-CH$_3$ | H | H |

TABLE 3-continued
(IV)
| No. | MW | A | B | R¹ | p | x | R² | R⁴ | R⁵ |
|---|---|---|---|---|---|---|---|---|---|
| 5-131 | 449.45 | 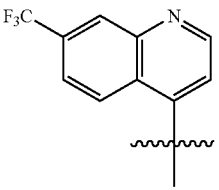 7-CF₃-quinolin-4-yl | S | H | 1 | 2 | 3-CH₃<br>4-CH₃ | H | H |
| 5-132 | 437.41 | 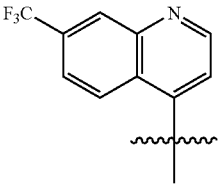 7-CF₃-quinolin-4-yl | S | 3-F | 1 | 1 | 4-CH₃ | H | H |
| 5-133 | 437.41 | 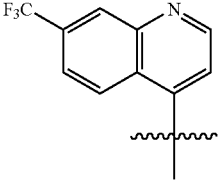 7-CF₃-quinolin-4-yl | S | 4-F | 1 | 1 | 3-CH₃ | H | H |
| 5-134 | 453.87 | 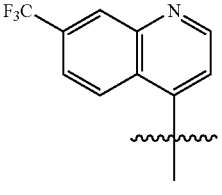 7-CF₃-quinolin-4-yl | S | 3-Cl | 1 | 1 | 4-CH₃ | H | H |
| 5-135 | 487.42 | 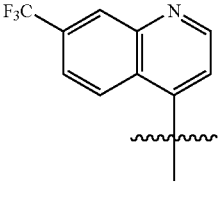 7-CF₃-quinolin-4-yl | S | 3-CF₃ | 1 | 1 | 5-CH₃ | H | H |
| 5-136 | 449.45 | 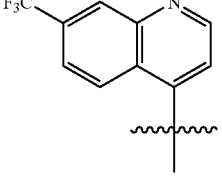 7-CF₃-quinolin-4-yl | S | H | 1 | 2 | 3-CH₃<br>5-CH₃ | H | H |

TABLE 3-continued (IV)

| No. | MW | A | B | R¹ | p | x | R² | R⁴ | R⁵ |
|---|---|---|---|---|---|---|---|---|---|
| 5-137 | 425.5 | 6-methoxy-2-methylquinolin-4-yl | S | H | 1 | 2 | 3-CH₃<br>4-CH₃ | H | H |
| 5-138 | 413.47 | 6-methoxy-2-methylquinolin-4-yl | S | 3-F | 1 | 1 | 4-CH₃ | H | H |
| 5-139 | 413.47 | 6-methoxy-2-methylquinolin-4-yl | S | 4-F | 1 | 1 | 3-CH₃ | H | H |
| 5-140 | 429.92 | 6-methoxy-2-methylquinolin-4-yl | S | 3-Cl | 1 | 1 | 4-CH₃ | H | H |
| 5-141 | 463.47 | 6-methoxy-2-methylquinolin-4-yl | S | 3-CF₃ | 1 | 1 | 4-CH₃ | H | H |
| 5-142 | 425.5 | 6-methoxy-2-methylquinolin-4-yl | S | H | 1 | 2 | 3-CH₃<br>5-CH₃ | H | H |

TABLE 3-continued (IV)

| No. | MW | A | B | R¹ | p | x | R² | R⁴ | R⁵ |
|---|---|---|---|---|---|---|---|---|---|
| 5-143 | 381.45 | quinolin-4-yl | S | H | 1 | 2 | 3-$CH_3$<br>5-$CH_3$ | H | H |
| 5-144 | 369.41 | quinolin-4-yl | S | 3-F | 1 | 1 | 4-$CH_3$ | H | H |
| 5-145 | 369.41 | quinolin-4-yl | S | 4-F | 1 | 1 | 3-$CH_3$ | H | H |
| 5-146 | 385.87 | quinolin-4-yl | S | 3-Cl | 1 | 1 | 4-$CH_3$ | H | H |
| 5-147 | 419.42 | quinolin-4-yl | S | 3-$CF_3$ | 1 | 1 | 4-$CH_3$ | H | H |
| 5-148 | 381.45 | quinolin-4-yl | S | H | 1 | 2 | 3-$CH_3$<br>5-$CH_3$ | H | H |

TABLE 3-continued (IV)

| No. | MW | A | B | R¹ | p | x | R² | R⁴ | R⁵ |
|---|---|---|---|---|---|---|---|---|---|
| 5-149 | 395.47 | 2-methylquinolin-4-yl | S | H | 1 | 2 | 3-CH₃ 4-CH₃ | H | H |
| 5-150 | 383.44 | 2-methylquinolin-4-yl | S | 3-F | 1 | 1 | 4-CH₃ | H | H |
| 5-151 | 383.44 | 2-methylquinolin-4-yl | S | 4-F | 1 | 1 | 3-CH₃ | H | H |
| 5-152 | 399.89 | 2-methylquinolin-4-yl | S | 3-Cl | 1 | 1 | 4-CH₃ | H | H |
| 5-153 | 433.45 | 2-methylquinolin-4-yl | S | 3-CF3 | 1 | 1 | 4-CH₃ | H | H |
| 5-154 | 395.47 | 2-methylquinolin-4-yl | S | H | 1 | 2 | 3-CH₃ 5-CH₃ | H | H |

TABLE 3-continued
(IV)
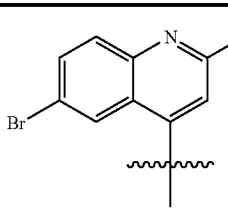
| No. | MW | A | B | R¹ | p | x | R² | R⁴ | R⁵ |
|---|---|---|---|---|---|---|---|---|---|
| 5-155 | 474.37 | 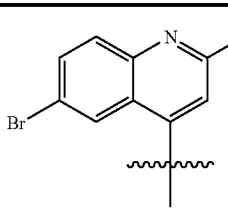 | S | H | 1 | 2 | 3-CH₃<br>4-CH₃ | H | H |
| 5-156 | 462.34 | 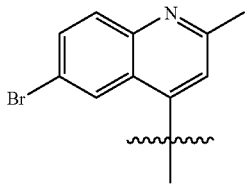 | S | 3-F | 1 | 1 | 4-CH₃ | H | H |
| 5-157 | 462.34 | 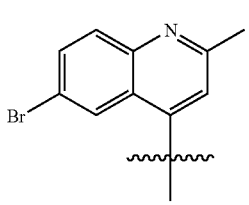 | S | 4-F | 1 | 1 | 3-CH₃ | H | H |
| 5-158 | 478.79 | 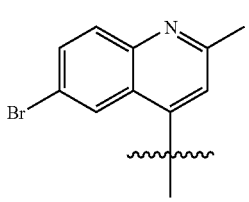 | S | 3-Cl | 1 | 1 | 4-CH₃ | H | H |
| 5-159 | 512.34 | 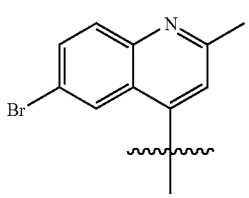 | S | 3-CF₃ | 1 | 1 | 5-CH₃ | H | H |
| 5-160 | 474.37 | 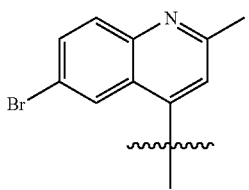 | S | H | 1 | 2 | 3-CH₃<br>5-CH₃ | H | H |

TABLE 3-continued (IV)

| No. | MW | A | B | R¹ | p | x | R² | R⁴ | R⁵ |
|---|---|---|---|---|---|---|---|---|---|
| 5-161 | 419.50 | 2-methylquinolin-4-yl | S | R¹ and R² taken together (see R₂) | 1 | 2 | 5-methyl-2-(methoxymethyl)furan-3-yl (fused) | H | H |
| 5-162 | 440.52 | 2-methylquinolin-4-yl | S | H | 1 | 3 | 3-CH₃ 4-CH₃ 5-CH₃ | CH₃ | H |
| 5-163 | 435.55 | 2-methylquinolin-4-yl | S | H | 1 | 2 | 3- cyclopropylmethyl 4-CH₃ | H | H |
| 5-164 | 441.50 | 2-methylquinolin-4-yl N-oxide | S | H | 1 | 3 | 3-CH₃ 4-CH₃ 5-CH₃ | H | H |
| 5-165 | 439.53 | 2-methylquinolin-4-yl | S | H | 2 | 3 | 3-CH₃ 4-CH₃ 5-CH₃ | H | H |
| 5-166 | 422.48 | 2-methylquinolin-4-yl | NR⁶ (R⁶ = CH₃) | H | 1 | 3 | 3-CH₃ 4-CH₃ 5-CH₃ | H | H |

TABLE 3-continued (IV)

| No. | MW | A | B | R¹ | p | x | R² | R⁴ | R⁵ |
|---|---|---|---|---|---|---|---|---|---|
| 5-167 | 454.54 | 4-(2-dimethylaminoquinolinyl) | S | H | 1 | 3 | 3-CH₃<br>4-CH₃<br>5-CH₃ | H | H |
| 5-168 | 361.42 | 4-pyridyl | S | H | 1 | 3 | 3-CH₃<br>4-CH₃<br>5-CH₃ | H | H |
| 5-169 | 362.41 | 4-pyrimidinyl | S | H | 1 | 3 | 3-CH₃<br>4-CH₃<br>5-CH₃ | H | H |
| 5-170 | 467.44 | 4-(2-methylquinolinyl) | S | H | 1 | 2 | 3-CHF₂<br>4-CHF₂ | H | H |
| 5-171 | 387.40 | 4-(2-methylquinolinyl) | S | 3-F<br>5-F | 1 | 1 | 4-H | H | H |
| 5-172 | 438.54 | 4-(2-methylquinolinyl) | S | 3-CH₂N(CH₃)₂ | 1 | 1 | 4-H<br>5-CH₃ | H | H |

TABLE 3-continued
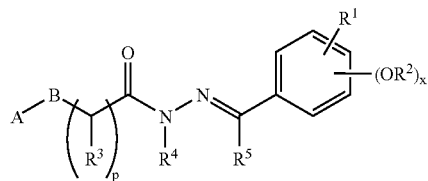
(IV)
| No. | MW | A | B | R¹ | p | x | R² | R⁴ | R⁵ |
|---|---|---|---|---|---|---|---|---|---|
| 5-173 | 401.43 | 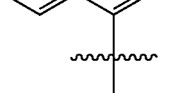 | S | 3-F 5-F | 1 | 1 | 4-$CH_3$ | H | H |
| 5-174 | 385.37 | 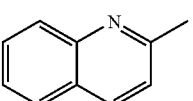 | O | 2-F 4-F | 1 | 1 | 3-$CH_3$ | H | H |
| 5-175 | 431.46 | 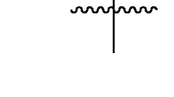 | S | 3-F 5-F | 1 | 1 | 4-$CH_3$ | H | H |
| 5-176 | 431.46 | 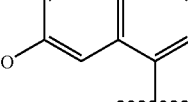 | S | 2-F 3-F | 1 | 1 | 4-$CH_3$ | H | H |
| 5-177 | 401.43 | 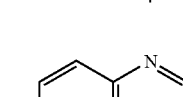 | S | 2-F 3-F | 1 | 1 | 4-$CH_3$ | H | H |
| 5-178 | 401.43 | 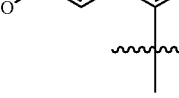 | S | 3-F 5-F | 1 | 1 | 4-$CH_3$ | H | H |

TABLE 3-continued
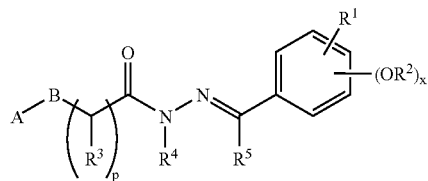
(IV)
| No. | MW | A | B | R¹ | p | x | R² | R⁴ | R⁵ |
|---|---|---|---|---|---|---|---|---|---|
| 5-179 | 387.40 | 4-quinolinyl | S | 3-F 5-F | 1 | 1 | 4-$CH_3$ | H | H |
| 5-180 | 381.45 | 4-quinolinyl | S | H | 1 | 2 | 3-$CH_3$ 4-$CH_3$ | H | H |
| 5-181 | 455.40 | 7-$CF_3$-4-quinolinyl | S | 2-F 3-F | 1 | 1 | 4-$CH_3$ | H | H |
| 5-182 | 455.40 | 7-$CF_3$-4-quinolinyl | S | 3-F 5-F | 1 | 1 | 4-$CH_3$ | H | H |
| 5-183 | 474.37 | 2-CH₃-4-quinolinyl | S | 4-Br | 1 | 2 | 3-$CH_3$ 5-$CH_3$ | H | H |
| 5-184 | 455.53 | 6-OCH₃-2-CH₃-4-quinolinyl | S | H | 1 | 3 | 3-$CH_3$ 4-$CH_3$ 5-$CH_3$ | H | H |

TABLE 3-continued
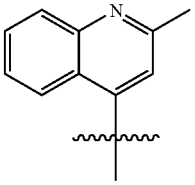
(IV)
| No. | MW | A | B | R¹ | p | x | R² | R⁴ | R⁵ |
|---|---|---|---|---|---|---|---|---|---|
| 5-185 | 425.5 | 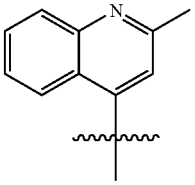 | S | H | 1 | 3 | 3-CH₃<br>4-CH₃<br>5-CH₃ | H | H |
| 5-186 | 459.95 | 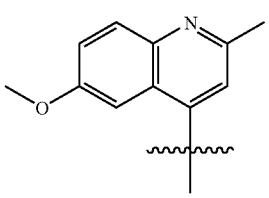 | S | 3-Cl | 1 | 2 | 4-CH₃<br>5-CH₃ | H | H |
| 5-187 | 429.92 | 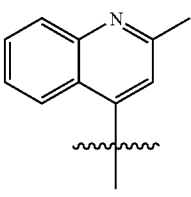 | S | 3-Cl | 1 | 2 | 4-CH₃<br>5-CH₃ | H | H |
| 5-188 | 504.4 | 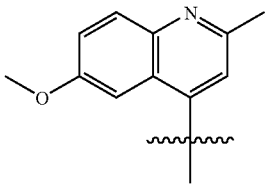 | S | 3-Br | 1 | 2 | 4-CH₃<br>5-CH₃ | H | H |
| 5-189 | 488.4 | 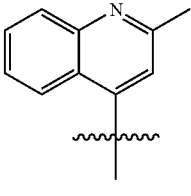 | S | 3-Br | 1 | 2 | 4-CH₃<br>5-CH₂CH₃ | H | H |
| 5-190 | 445.92 | 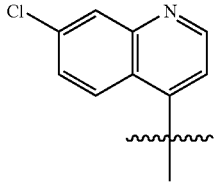 | S | H | 1 | 3 | 3-CH₃<br>4-CH₃<br>5-CH₃ | H | H |

TABLE 3-continued
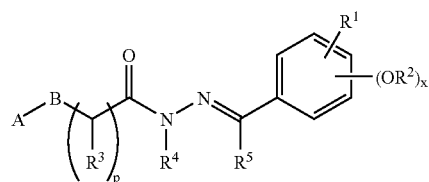
(IV)
| No. | MW | A | B | R¹ | p | x | R² | R⁴ | R⁵ |
|---|---|---|---|---|---|---|---|---|---|
| 5-191 | 413.47 | 2-methylquinolin-4-yl | S | 3-F | 1 | 2 | 4-CH₃<br>5-CH₃ | H | H |
| 5-192 | 474.37 | 2-methylquinolin-4-yl | S | 2-Br | 1 | 2 | 4-CH₃<br>5-CH₃ | H | H |
| 5-193 | 413.47 | 6-methoxy-2-methylquinolin-4-yl | S | 4-F | 1 | 1 | 3-CH₃ | H | H |
| 5-194 | 379.48 | 2-methylquinolin-4-yl | S | 4-CH₃ | 1 | 1 | 3-CH₃ | H | H |
| 5-195 | 460.34 | quinolin-4-yl | S | 3-Br | 1 | 2 | 4-CH₃<br>5-CH₃ | H | H |
| 5-196 | 528.34 | 8-(trifluoromethyl)quinolin-4-yl | S | 3-Br | 1 | 2 | 4-CH₃<br>5-CH₃ | H | H |

TABLE 3-continued
(IV)
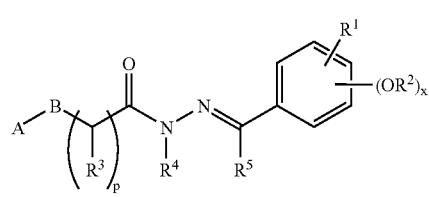
| No. | MW | A | B | R¹ | p | x | R² | R⁴ | R⁵ |
|---|---|---|---|---|---|---|---|---|---|
| 5-197 | 411.47 | 4-quinolinyl | S | H | 1 | 3 | 3-$CH_3$<br>4-$CH_3$<br>5-$CH_3$ | H | H |
| 5-198 | 413.47 | 2-methyl-4-quinolinyl | S | 2-F | 1 | 2 | 4-$CH_3$<br>5-$CH_3$ | H | H |
| 5-199 | 460.34 | 8-quinolinyl | S | 3-Br | 1 | 2 | 4-$CH_3$<br>5-$CH_3$ | H | H |
| 5-200 | 429.92 | 2-methyl-4-quinolinyl | S | 2-Cl | 1 | 2 | 4-$CH_3$<br>5-$CH_3$ | H | H |
| 5-201 | 381.45 | 8-quinolinyl | S | 3-Cl | 1 | 2 | 4-$CH_3$<br>5-$CH_3$ | H | H |
| 5-202 | 433.45 | 2-methyl-4-quinolinyl | S | 4-$CF_3$ | 1 | 1 | 3-$CH_3$ | H | H |

TABLE 3-continued
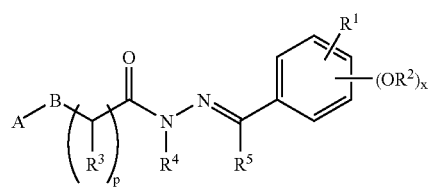
(IV)
| No. | MW | A | B | R¹ | p | x | R² | R⁴ | R⁵ |
|---|---|---|---|---|---|---|---|---|---|
| 5-203 | 483.89 | 8-CF₃-quinolin-4-yl | S | 3-Cl | 1 | 2 | 4-CH₃, 5-CH₃ | H | H |
| 5-204 | 483.58 | 6-methoxy-2-methyl-3-ethyl-quinolin-4-yl | S | H | 1 | 3 | 3-CH₃, 4-CH₃, 5-CH₃ | H | H |
| 5-205 | 460.34 | isoquinolin-1-yl | S | 3-Br | 1 | 2 | 4-CH₃, 5-CH₃ | H | H |
| 5-206 | 429.92 | 2-methyl-quinolin-4-yl | S | 2-Cl | 1 | 2 | 3-CH₃, 4-CH₃ | H | H |
| 5-207 | 474.37 | 2-methyl-quinolin-4-yl | S | 2-Br | 1 | 2 | 3-CH₃, 4-CH₃ | H | H |
| 5-208 | 443.95 | 2-methyl-quinolin-4-yl | S | 3-Cl | 1 | 2 | 4-CH₃, 5-CH₂CH₃ | H | H |

TABLE 3-continued
(IV)
| No. | MW | A | B | R¹ | p | x | R² | R⁴ | R⁵ |
|---|---|---|---|---|---|---|---|---|---|
| 5-209 | 399.89 | 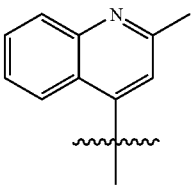 | S | 4-Cl | 1 | 1 | 3-CH₃ | H | H |
| 5-210 | 444.34 | 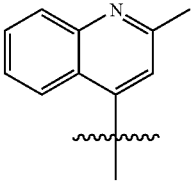 | S | 4-Br | 1 | 1 | 3-CH₃ | H | H |
| 5-211 | 411.47 | 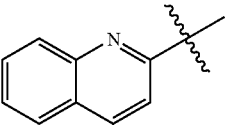 | S | H | 1 | 3 | 3-CH₃<br>4-CH₃<br>5-CH₃ | H | H |
| 5-212 | 409.46 | 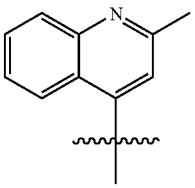 | S | H | 1 | 3 | 3-OCH₂O-4<br>5-CH₃ | H | H |
| 5-213 | 423.53 | 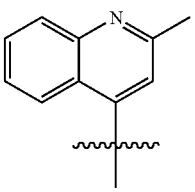 | S | H | 1 | 2 | 3-iso-propyl<br>4-CH₃ | H | H |

Example 6

(E)-3-(1-BENZYL-1H-BENZO[D]IMIDAZOL-2-YL)-N'-(3,4-DIMETHOXYBENZYLIDENE)PROPANEHYDRAZIDE

Step 6A Preparation of ethyl 3-(1H-benzo[d]imidazol-2-yl)propanoate 6a

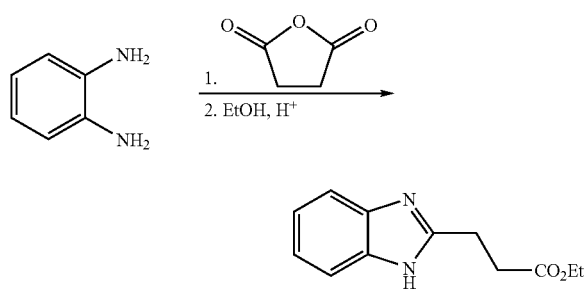

To a stirred solution of benzene-1,2-diamine (20.0 g, 0.19 mol, 1.0 eq.) in dioxane (500 mL) at room temperature, was added succinic anhydride (22.2 g, 0.22 mol, 1.2 eq.), and the reaction mixture was heated to 80° C. and stirred at that temperature for 16 hours. The resulting precipitate was filtered and washed with dioxane (100 mL), water (100 mL) and diethyl ether (100 mL) to give a white solid. The solid was suspended in ethanol (400 mL), and concentrated sulfuric acid (10 mL) was added at room temperature. The reaction mixture was heated to reflux and stirred at that temperature for 20 hours. The reaction was then cooled to room temperature and concentrated in vacuo. Water (100 mL) was added, and the mixture was adjusted to pH 7 with 1 M aqueous NaOH solution. The aqueous layer was extracted into ethyl acetate (3×100 mL), and the combined organic extracts were dried over magnesium sulfate and concentrated in vacuo to give 6a as a pale-orange oil (15.6 g, 46%).

Step 6B Preparation of ethyl 3-(1-benzyl-1H-benzo[d]imidazol-2-yl)propanoate 6b

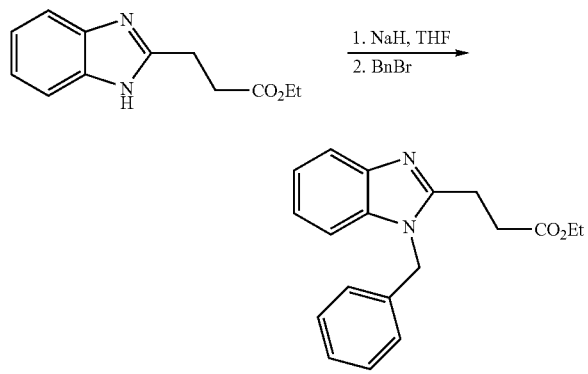

To a stirred solution of ethyl 3-(1H-benzo[d]imidazol-2-yl)propanoate 6a (2.85 g, 13.1 mmol, 1.0 eq.) in tetrahydrofuran (100 mL) at 0° C., was added 60% sodium hydride in mineral oil (784 mg, 19.6 mmol, 1.5 eq.), and the reaction was stirred at 0° C. for 20 minutes. Benzyl bromide (4.47 g, 26.1 mmol, 2.0 eq.) was added at 0° C., and the reaction was stirred, with warming to room temperature, for 16 hours. The mixture was concentrated in vacuo and water (100 mL) was carefully added. The aqueous layer was extracted with dichloromethane (3×75 mL), and the combined organic extracts were washed with 1M hydrochloric acid (100 mL) and brine (100 mL). The organic layer was dried over magnesium sulfate and concentrated in vacuo. Purification by flash chromatography (5% MeOH:95% EtOAc) gave 6b as an orange oil (3.32 g, 82%).

Step 6C Preparation of 3-(1-benzyl-1H-benzo[d]imidazol-2-yl)propanehydrazide 6c

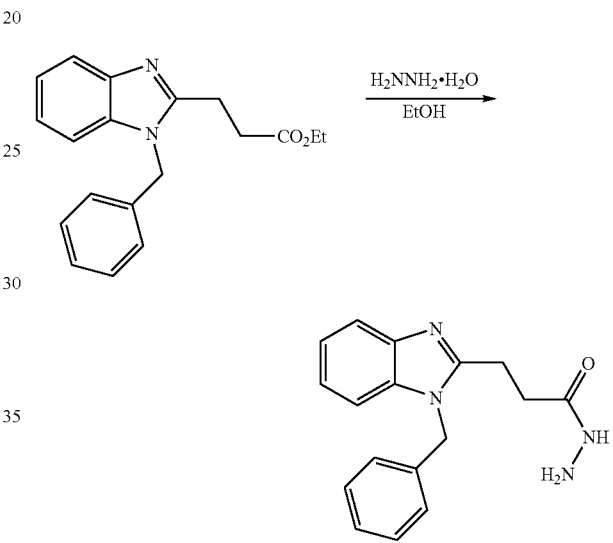

Step 6C was performed in an analogous fashion to Example 4, Step 4C.

Step 6D Preparation of (E)-3-(1-benzyl-1H-benzo[d]imidazol-2-yl)-N'-(3,4-dimethoxybenzylidene)propanehydrazide 6-1

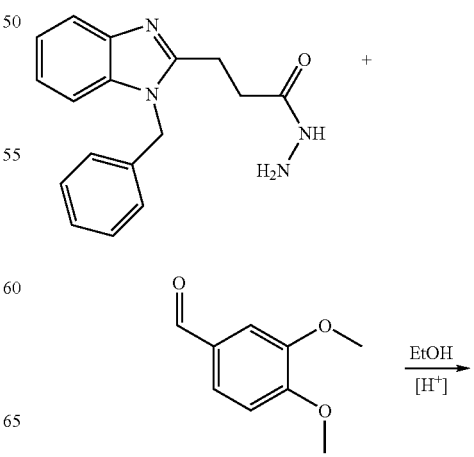

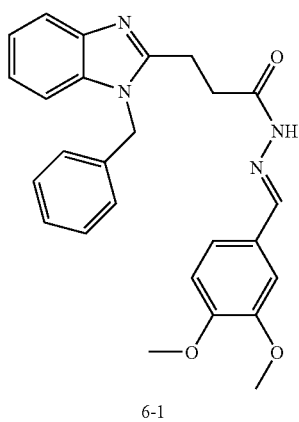

6-1

Step 6D was prepared in an analogous fashion to Example 4, Step 4D.

Referring to Table 4, the following derivatives of structure (V), wherein R, $R^3$, $R^4$ and $R^5$ are hydrogen, were synthesized according to the procedures outlined in Example 6

TABLE 4

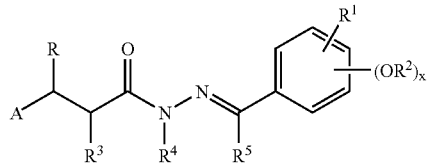

(V)

| No. | MW | A | $R^1$ | x | $R^2$ |
|---|---|---|---|---|---|
| 6-1 | 442.52 | 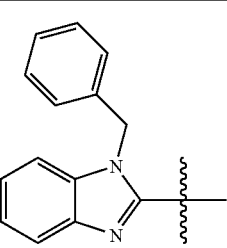 | H | 2 | 3-$CH_3$<br>4-$CH_3$ |
| 6-2 | 382.42 | 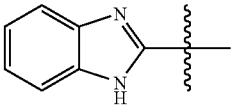 | H | 2 | 3-$CH_3$<br>4-$CH_3$<br>5-$CH_3$ |
| 6-3 | 387.44 | 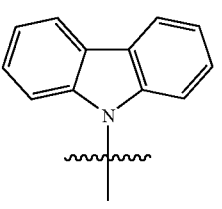 | H | 2 | 3-$CH_3$<br>4-H |
| 6-4 | 320.39 | 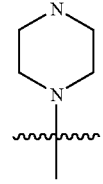 | H | 2 | 3-H<br>4-$CH_3$ |
| 6-5 | 336.35 | 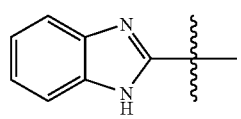 | H | 2 | 3-$CH_2$-4 |
| 6-6 | 338.37 | 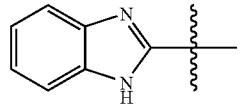 | H | 2 | 3-H<br>4-$CH_3$ |
| 6-7 | 352.39 | 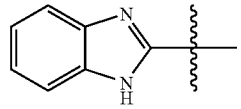 | H | 2 | 3-$CH_2CH_3$<br>4-H |
| 6-8 | 382.42 | 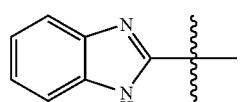 | H | 3 | 2-$CH_3$<br>3-$CH_3$<br>4-$CH_3$ |
| 6-9 | 382.42 | 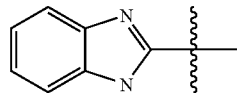 | H | 3 | 2-$CH_3$<br>4-$CH_3$<br>5-$CH_3$ |
| 6-10 | 370.38 | 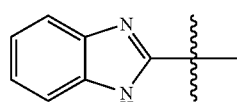 | 2-F | 2 | 4-$CH_3$<br>5-$CH_3$ |
| 6-11 | 458.52 | 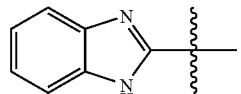 | H | 3 | 3-$CH_3$<br>4-benzyl<br>5-$CH_3$ |
| 6-12 | 456.55 | 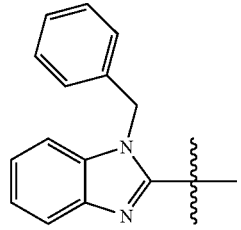 | H | 2 | 3-$CH_3$<br>4-$CH_2CH_3$ |

TABLE 4-continued (V) structure with R, R³, R⁴, R⁵ substituents and (OR²)ₓ on phenyl ring attached via N-N=C(R⁵)

| No. | MW | A | R¹ | x | R² |
|---|---|---|---|---|---|
| 6-13 | 456.55 | 1-benzyl-benzimidazol-2-yl | H | 2 | 3-CH₂CH₃ 4-CH₃ |

Example 7

Referring to Table 5, the following derivatives of structure (IV), wherein R⁴ and R⁵ are hydrogen, can be synthesized according to Reaction Scheme 5.

TABLE 5

(VI) structure with R⁴, R⁵ on N and (OR²)ₓ on phenyl ring

| No. | MW | A | R¹ | x | R² |
|---|---|---|---|---|---|
| 7-1 | 304.30 | 2-furyl | H | 3 | 3-CH₃ 4-CH₃ 5-CH₃ |
| 7-2 | 380.40 | 2-furyl | H | 2 | 3-CH₃ 4-benzyl 5-CH₃ |
| 7-3 | 272.26 | 2-pyrazinyl | H | 2 | 3-CH₃ 4-H |
| 7-4 | 271.28 | 2-pyridyl | H | 2 | 3-H 4-CH₃ |
| 7-5 | 323.35 | 1H-indol-3-yl | H | 2 | 3-CH₂CH₃ 4-H |
| 7-6 | 328.32 | 2,3-dihydro-1,4-benzodioxin-2-yl | H | 2 | 3-CH₃ 4-H |
| 7-7 | 328.32 | 2,3-dihydro-1,4-benzodioxin-2-yl | H | 2 | 3-H 4-CH₃ |
| 7-8 | 258.23 | 2-furyl | H | 2 | 3-CH₂-4 |
| 7-9 | 260.25 | 2-furyl | H | 2 | 3-H 4-CH₃ |
| 7-10 | 274.28 | 2-furyl | H | 2 | 3-CH₂CH₃ 4-H |
| 7-11 | 304.30 | 2-furyl | H | 3 | 2-CH₃ 3-CH₃ 4-CH₃ |

TABLE 5-continued (VI) Structure: A-C(=O)-N(R4)-N=C(R5)-(phenyl with R1 and (OR2)x)

| No. | MW | A | R¹ | x | R² |
|---|---|---|---|---|---|
| 7-12 | 304.30 | 2-furyl | H | 3 | 2-$CH_3$, 4-$CH_3$, 5-$CH_3$ |
| 7-13 | 292.27 | 2-furyl | 2-F | 2 | 4-$CH_3$, 5-$CH_3$ |
| 7-14 | 340.28 | 2-furyl | H | 3 | 3-$CH_3$, 4-$CHF_2$, 5-$CH_3$ |
| 7-15 | 347.33 | 2-furyl | H | 3 | 3-$CH_3$, 4-$CH_2CONH_2$, 5-$CH_3$ |

Example 8

Compound Assay

PDE10 Biochemical Assay

The phosphodiesterase (PDE) assay was performed using recombinant human PDE1A3, 2A3, 3 catalytic region, 4 catalytic region, 5 catalytic region, 7A, 8A, 9A2, 10A1 and 11A1 enzymes expressed in a baculoviral system using Sf9 cells. PDE activity was measured using a modification of the two-step method of Thompson and Appleman described above which was adapted for 96 well plate format. The effect of the PDE inhibitors was determined by assaying a fixed amount of the enzyme in the presence of test compound concentrations and a substrate concentration below that of the Km, so that Ki equals $IC_{50}$. The final assay volume was 110 μl with assay buffer (10 mM $MgCl_2$; 40 mM Tris.HCl; pH 7.4). Reactions were initiated with enzyme and incubated with ($^3$H)-substrate and substance for 20 minutes at 30° C. The reaction was terminated by denaturing the enzyme (heating the reaction to 70° C. for 2 minutes). The reaction was then cooled at 4° C. for 10 minutes before the addition of snake venom (*Crotalus atrox*, 0.2 mg/ml) for 10 minutes at 30° C., thus allowing non-specific hydrolysis of the tritiated substrate. Separation of the remaining unhydrolysed cyclic nucleotide was achieved by a batch binding of the mixture to activated Dowex (200 μl) anion exchange resin. The anion exchange resin bound the charged nucleotides, leaving only hydrolysed (3H) substrate in the soluble fraction. The soluble fraction (50 μl) was then added to microscint-20 (200 μl) and counted on a Top Count Plate reader. Radioactivity units were plotted against inhibitor concentration and $IC_{50}$ values obtained using Graph Pad Prism software.

Alternatively, phosphodiesterase activity was measured by scintillation proximity assay (SPA) with [$^3$H]-cGMP as substrate. Purified PDE10 was diluted and stored in 25 mM Tris-Cl (pH 8.0)/100 mM NaCl/0.05% Tween 20/50% glycerol/3 mM DTT. Assays contained (final concentrations): 50 mM Tris-Cl (pH 7.5)/8.3 mM $MgCl_2$/1.7 mM EGTA/0.5 mg/ml BSA/5% DMSO and 2 ng PDE10 in a final volume of 0.1 mL. Inhibition was evaluated at 8 concentrations in duplicate. Reactions were initiated by addition of enzyme and were terminated after 20 minutes at 300 by the addition of 50 μl of SPA beads containing $Zn^{++}$. The mixture was shaken, allowed to settle for 3 hours, and counted in a Wallac plate counter. Results (net cpm) were fitted to a four parameter logistic model using Excel Solver®.

Further, the inhibition of other PDE enzymes by the PDE10 inhibitors was evaluated under the same conditions described above for PDE10 except the amount of enzyme added was optimized for each PDE. Fractional inhibition was evaluated at four concentrations (0.1, 1, 10, and 100 μM). In cases where inhibition at the highest concentration was less than 50%, the lower limit value in the logistic model was fixed to 0% activity.

In the above assays, compounds of this invention are PDE10 inhibitors with an $IC_{50}$ of 100 μM or less, generally less than 10 μM, and typically less than 1 μM. To this end, compounds 1-1, 2-2, 4-1, 5-1, 5-2, 5-3, 5-4, 5-5, 5-25, 5-26, 5-27, 5-64, 5-67, 5-73, 5-75, 5-76, 5-77, 5-79, 5-91, 5-92, 5-104, 5-105, 5-108, 5-109, 5-110, 5-111, 5-112, 5-114, 5-115, 5-118, 5-119, 5-121, 5-122, 5-123, 5-125, 5-129, 5-130, 5-161, 5-162, 5-163, 5-183, 5-184, 5-185, 5-186, 5-187, 5-188, 5-189, 5-190, 5-191, 5-192, 5-193, 5-194, 5-195, 5-196, 5-197, 5-198, 5-199, 5-200, 5-201, 5-202, 5-203, 5-204, 5-205, 5-208, 5-209, 5-210, 5-211, 5-212, and 5-213 were found to have $IC_{50}$'s of less than or equal to 1 μM.

Examples 9-15

Evaluation of Representative Compounds in Behavioral Models

Schizophrenia has been associated with dysfunctions of dopaminergic, glutamatergic and serotonergic neurotransmission. Psychostimulant drugs in these three classes, dopaminergic agonists (such as amphetamine and apomorphine), glutamatergic antagonists (such as PCP and ketamine), and serotonergic agonists (such as LSD and MDMA), all induce psychotomimetic states (e.g., hyperactivity and disruption of prepulse inhibition) in animals that closely resemble schizophrenia symptoms in humans. Known antipsychotic drugs, including both typical antipsychotics (e.g., haloperidol) and atypical antipsychotics (e.g., olanzapine), reverse such psychotomimetic states in animals. Examples 9-14 described below evaluate representative compounds of the present invention in animal behavioral models to compare the resulting effect to that of known antipsychotics. Methods used in the Examples 9-14 are as follows:

Prepulse inhibition (PPI) of the acoustic startle response evaluates the brain's sensorimotor gating function that is often disrupted in schizophrenic and other psychotic conditions. Psychostimulants such as PCP and amphetamine reduce or disrupt PPI, and many antipsychotics increase PPI and/or reverse psychostimulant-induced reduction of PPI. In addition, the startle response to the loud noise itself (in the absence of any prepulse) is a measure of the basic sensorimotor reflex. The test is done using the SR-Lab System (San Diego Instruments, San Diego, Calif.). A test session consists of six trial types under the background noise of 70 dB. One type uses a 40 msec, 120 dB noise as the startle stimulus. Four types contain acoustic startle stimulus preceded by acoustic prepulses of different intensity: the 20-msec prepulse noise of 73, 76, 79, or 82 dB is presented 100 msec before the 120 dB startle stimulus. The last trial type uses the 70 dB background noise with no startle stimulus to measure baseline reaction. Six blocks of the six trial types are presented in pseudorandom order. The startle response is recorded for 65 ms starting with the onset of the startle stimulus. Measurements used to assess PPI are the maximum startle amplitude and the percent each of the 4 prepulses inhibits the startle response.

Psychostimulant-induced hyperactivity is measured by injecting animals with PCP or amphetamine and monitoring the animals' activity levels in the VersaMax chambers (Accuscan Instruments, Columbus, Ohio) measuring 40×40 cm. Locomotor activity is detected by photobeam breaks as the animal crosses each beam. The animal is placed in the center of the field and left undisturbed for a period of time (20 min to 2 hr) to measure its spontaneous activity in a novel environment. Measurements used to assess locomotor activity include: horizontal activity, total distance traveled, vertical activity (rearing events—animal raises up on hindlimbs), rotation, stereotypy, and distance traveled in the center compared to total distance traveled (center:total distance ratio). Psychostimulants, including dopamine agonist amphetamine and NMDA antagonist PCP, induce psychosis-like conditions manifested as hyperactivity and increased stereotypic behavior. Known antipsychotics are able to reverse psychostimulant-induced hyperactivity and increased stereotypy.

Conditioned avoidance response (CAR) is a behavioral test to evaluate antipsychotic effect of a test compound. It utilizes a shuttle box (Med Associates, St. Albans, Vt.) with two equal chambers separated by a retractable door. Each chamber is fitted with metal grid floor that is capable of delivering electric shocks independently. A computer program is used to implement the testing paradigm as well as record the animal's movement between the two chambers through infrared beam sensors. The testing paradigm is as the follows. A mouse is placed into one chamber. A light (conditioned stimulus, CS) comes on. Five seconds later, mild electric shocks (0.4 mA) (unconditioned stimulus, US) are delivered to the chamber where the mouse is located (as detected by infrared beams) until the mouse escapes to the adjacent chamber or until 10 sec has elapsed. The US and CS always co-terminate. With randomized inter-trial intervals averaging 15 sec, 30 such CS-US pairing trials are given to each mouse each day. For each trial, an escape response is registered if the mouse crosses to the other chamber after being shocked (i.e., during the 10-sec US period), and an avoidance response is registered if the mouse crosses to the other chamber during the first 5-sec CS only period. The animals are trained in such paradigm for 15-20 days, during which the average percentage of avoidance responses will improve to 60-80%. This indicates that animals have learned to avoid the onset of footshocks by moving to the opposite chamber upon activation of the CS (light). These trained animals are then used for compound testing using the same paradigm. Known antipsychotics have been found to inhibit the conditioned avoidance response, and the ability of new compounds to inhibit this response is thought to be predictive of antipsychotic effect in humans.

The antipsychotic effect of a test compound may also be evaluated by a novel object recognition test. In a novel object recognition test, mice are housed singly for 1-2 days and then injected with vehicle, PCP, or PCP plus the test compound. Twenty minutes after injection, the mice are presented with and allowed to explore two identical objects for 30 minutes. At the end of the exploration period the objects are removed. Twenty-four hours later each mouse is presented with a pair of objects, one familiar and one novel. After a variable delay, the mice begin to explore the objects. The time exploring each object is measured for 4 minutes starting from the first approach to either object. The fraction of total exploration time spent studying the novel object is recorded as a measure of novelty recognition.

Example 9

Increased Prepulse Inhibition for Compound 5-1

Compound 5-1 (Table 3) was found to increase prepulse inhibition (PPI) similar to olanzapine, as shown in FIG. 1. C57BL/6 male mice were injected intraperitoneally (i.p.) with either compound or vehicle. Thirty minutes after injection, the mice were transferred to the PPI testing chamber and evaluated. FIG. 1A shows that olanzapine (3 mg/kg) significantly decreases the startle response (left panel) and increases PPI at 3 different prepulse levels (right panel) compared to vehicle control (* $p<0.05$, n=8 per group, student's t-test). FIG. 1B shows that compound 5-1 (50 mg/kg) does not affect the startle response (left panel) but significantly increases PPI at 3 different prepulse levels (right panel) compared to vehicle control (* $p<0.05$, ** $p<0.01$, n=24 per group, student's t-test).

Example 10

Reduction of PCP-Induced Hyperactivity for Compound 5-1

Figure 2:
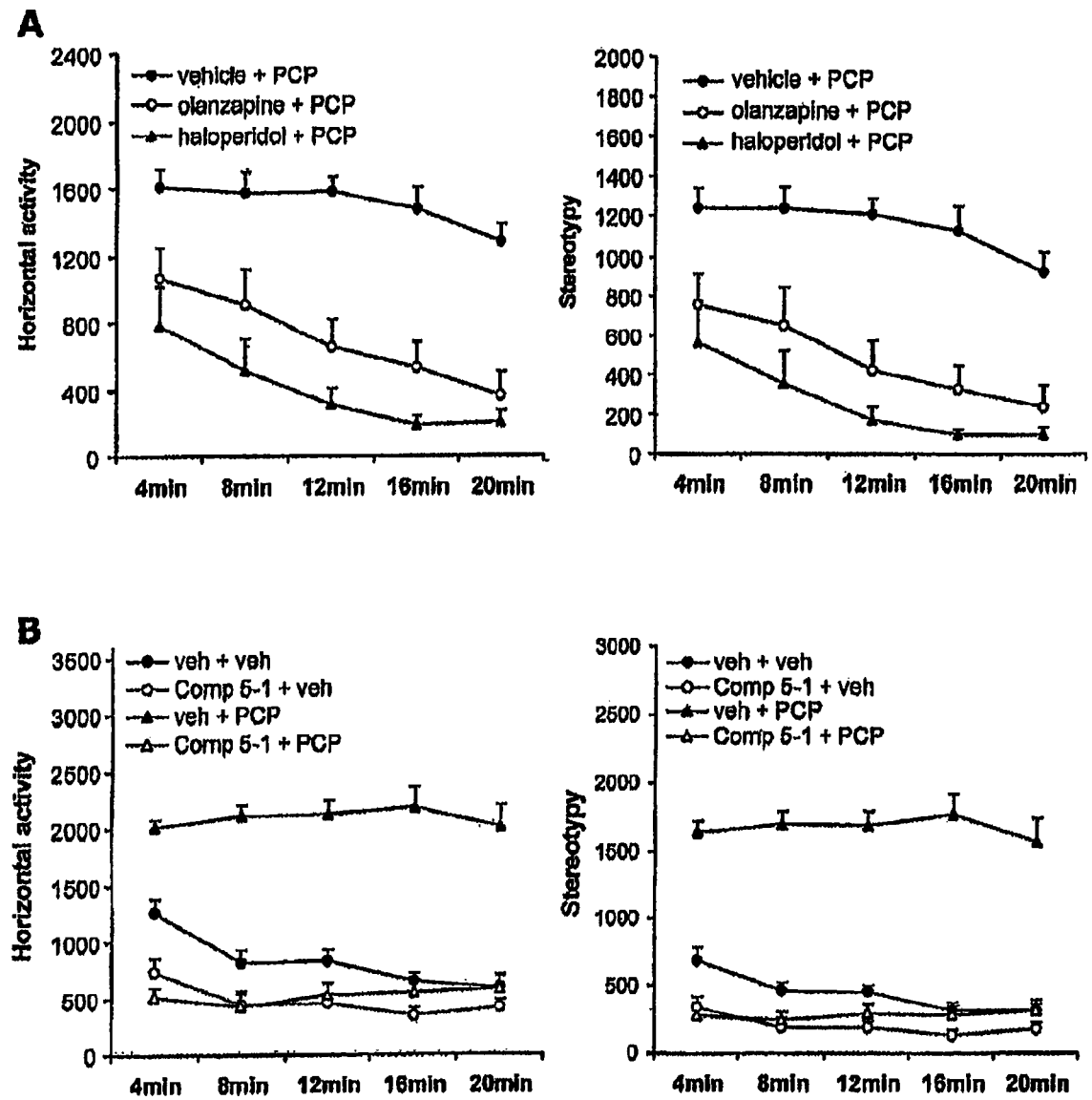
FIG. 2 illustrates that compound 5-1 (Table 3) reduces PCP-induced hyperactivity similar to olanzapine and haloperidol as described in Example 10.

Compound 5-1 (Table 3) was found to reduce PCP-induced hyperactivity similar to olanzapine and haloperidol, as shown in FIG. 2. C57BL/6 male mice were injected with either compound or vehicle via i.p. Ten minutes later, the mice were injected with PCP (5 mg/kg) (or vehicle as in FIG. 2B) via i.p. The mice were placed in the activity chambers 10 minutes after PCP injection and their locomotor activities were monitored by infrared beam breaks for 20 min. FIG. 2A shows that both olanzapine (0.2 mg/kg) and haloperidol (0.2 mg/kg) significantly reduce the hyperactivity (left panel) and stereotypy (right panel) induced by PCP as seen in the vehicle+PCP control ($p<0.001$, n=8 per group, repeated measures ANOVA). FIG. 2B shows that compound 5-1 (50 mg/kg) completely abolishes the hyperactivity (left panel) and stereotypy (right panel) induced by PCP as seen in the vehicle+PCP control ($p<0.001$, n=8 per group, repeated measures ANOVA).

Example 11

Reduction of Amphetamine-Induced Hyperactivity for Compound 5-1

Figure 3:
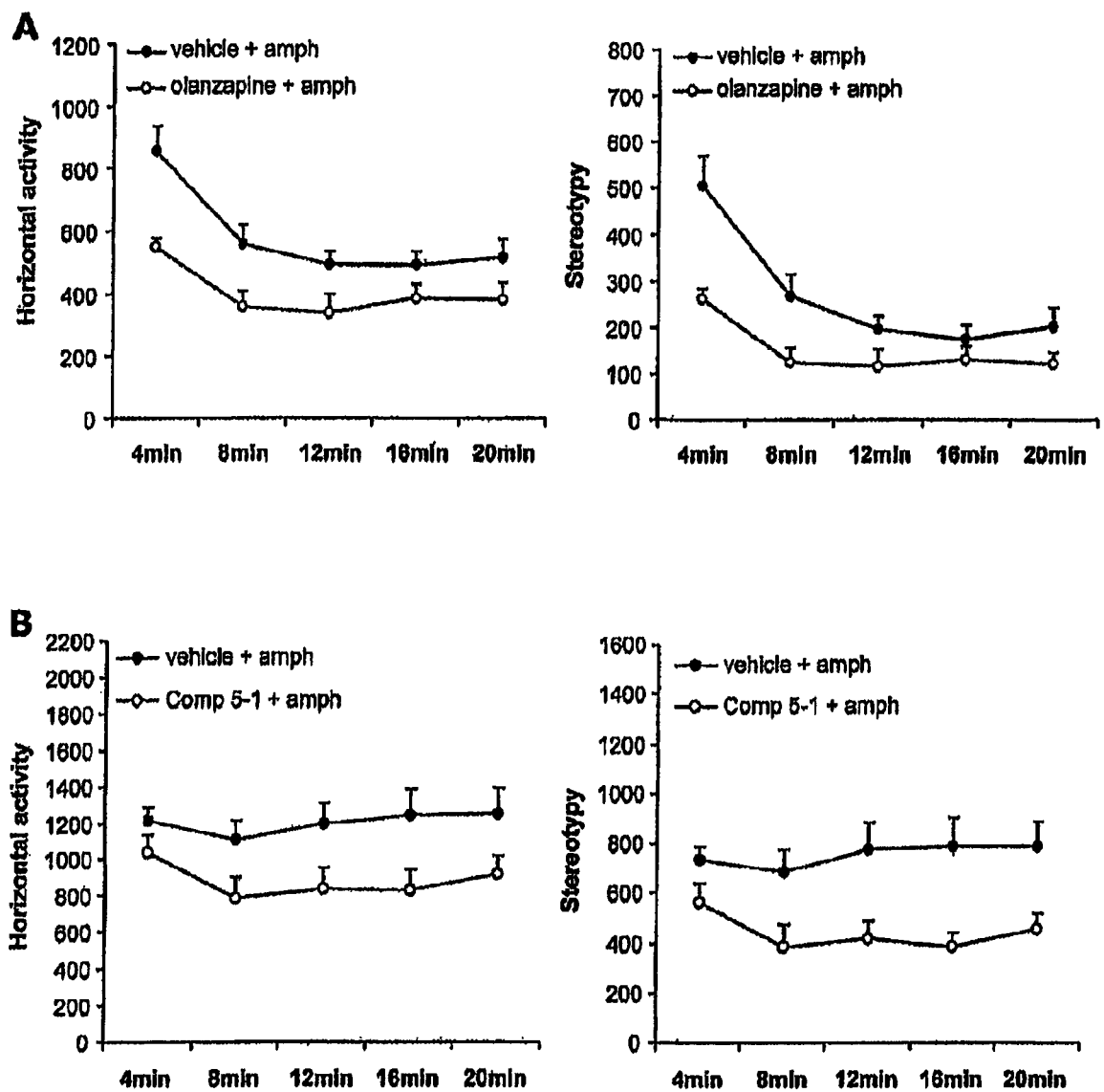
FIG. 3 illustrates that compound 5-1 (Table 3) reduces amphetamine-induced hyperactivity similar to olanzapine, as described in Example 11.

Compound 5-1 (Table 3) was found to reduce amphetamine-induced hyperactivity similar to olanzapine, as shown in FIG. 3. C57BL/6 male mice were injected with either compound or vehicle via i.p. Ten minutes later, the mice were injected with amphetamine (2 mg/kg in (FIG. 3A) or 5 mg/kg in (FIG. 3B)) via i.p. The mice were placed in the activity chambers 10 minutes after amphetamine injection and their locomotor activities were monitored by infrared beam breaks for 20 min. FIG. 3A shows that olanzapine (0.2 mg/kg) partially but significantly reduce the hyperactivity (left panel) and stereotypy (right panel) induced by amphetamine ("amph") as seen in the vehicle+amph control ($p<0.05$, n=8 per group, repeated measures ANOVA). FIG. 3B shows that compound 5-1 (50 mg/kg) also partially but significantly reduce the hyperactivity (left panel) and stereotypy (right panel) induced by amphetamine as seen in the vehicle+amph control ($p<0.01$, n=8 per group, repeated measures ANOVA).

Example 12

Reduction of Conditioned Avoidance Response for Compound 5-1

Figure 4:
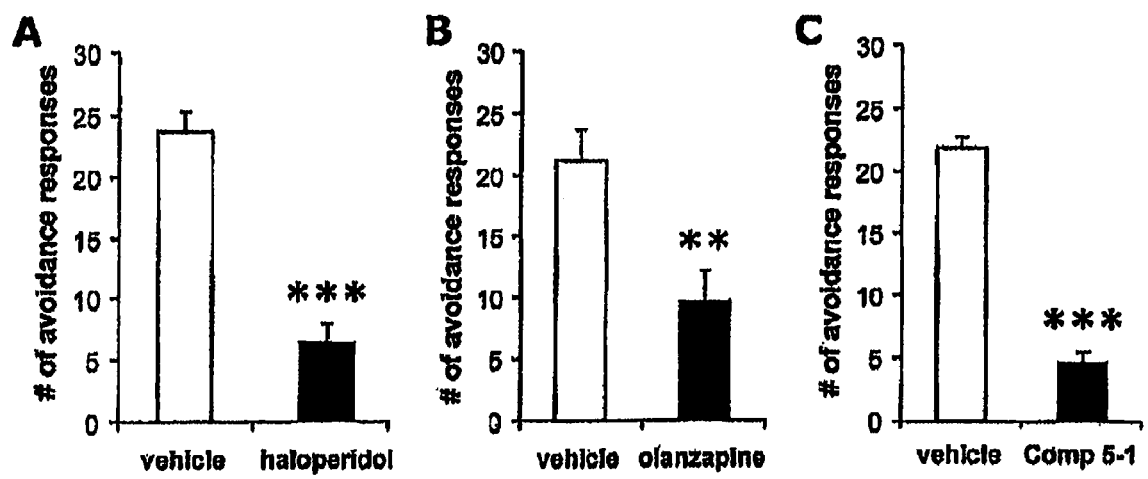
FIG. 4 illustrates that compound 5-1 (Table 3) reduces Conditioned Avoidance Response (CAR) similar to haloperidol and olanzapine, as described in Example 12.

Compound 5-1 (Table 3) was found to reduce Conditioned Avoidance Response (CAR) similar to haloperidol and olanzapine, as shown in FIG. 4. C57BL/6 male mice were trained in the CAR paradigm to predict and avoid the noxious stimulus, reaching a plateau of approximately 20-25 avoidance responses per 30 trials ("training plateau") each day. The mice were then injected with compound or vehicle via i.p., and 20 minutes later they were tested for 30 trials in the CAR paradigm. Vehicle treatment and compound treatment were given to the same animals on alternating days, and the effect of compound in reducing avoidance response was analyzed through within-subject comparison (paired t-test). Vehicle exposure ("vehicle") does not alter the avoidance response of these trained animals. FIG. 4A shows that haloperidol (0.15 mg/kg) significantly reduces the number of avoidance response (* $p<0.001$, n=6 per group, paired t-test). FIG. 4B shows that olanzapine (0.45 mg/kg) significantly reduces the number of avoidance response ( $p<0.01$, n=6 per group, paired t-test). FIG. 4C shows that compound 5-1 (30 mg/kg) significantly reduces the number of avoidance response (*** $p<0.001$, n=6 per group, paired t-test). In all these cases, the numbers of escape response increase correspondingly and the total numbers of transitions between the two chambers do not change (data not shown), indicating a specific reduction of CAR that is not due to compromised motor function.

Example 13

Reduction of Conditioned Avoidance Response and Hyperactivity for Compound 5-110

Figure 5:
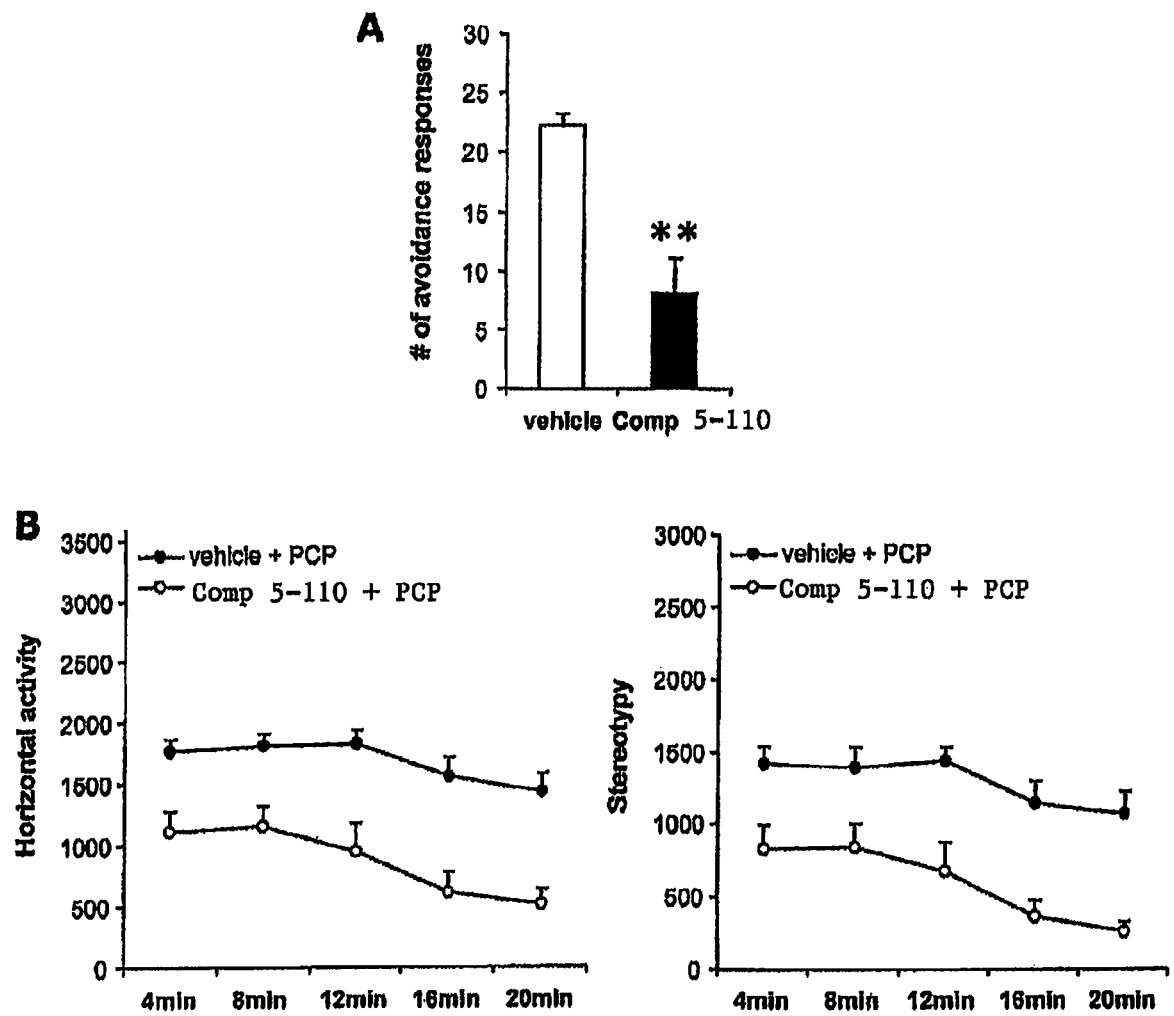
FIG. 5 illustrates that compound 5-110 (Table 3) exhibits antipsychotic properties in two behavioral tests, as described in Example 13.

Compound 5-110 (Table 3) was found to exhibit antipsychotic properties in two behavioral tests, as shown in FIG. 5. FIG. 5A shows that compound 5-110 (10 mg/kg) significantly reduces the number of avoidance response in the CAR test (** $p<0.01$, n=6 per group, paired t-test). Experimental procedure was the same as in Example 12. FIG. 5B shows that compound 5-110 (30 mg/kg) significantly reduces the hyperactivity (left panel) and stereotypy (right panel) induced by PCP (5 mg/kg) ($p<0.001$, n=8 per group, repeated measures ANOVA). Experimental procedure was the same as in Example 10.

Example 14

Reduction of Conditioned Avoidance Response for Compound 5-103

Figure 6:
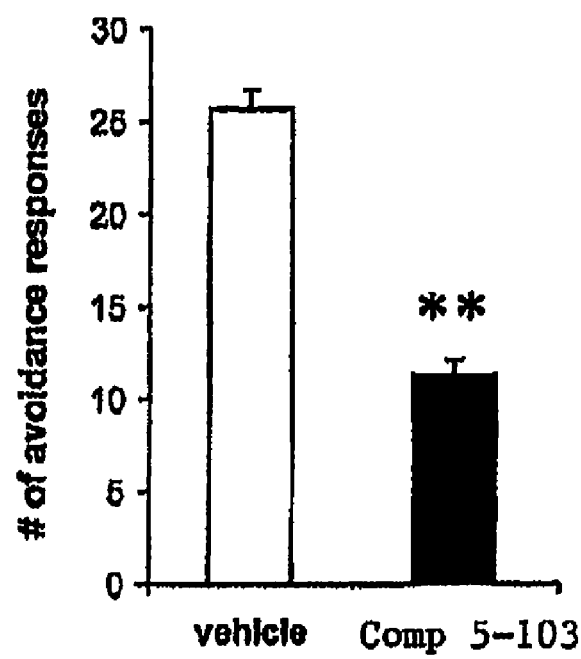
FIG. 6 illustrates that compound 5-103 (Table 3) reduces Conditioned Avoidance Response (CAR), as described in Example 14. Compound 5-103 (10 mg/kg) significantly reduces the number of avoidance response (** $p<0.01$, n=6 per group, paired t-test).

Compound 5-103 (Table 3) was found to reduce Conditioned Avoidance Response (CAR), as shown in FIG. 6. Compound 5-103 (10 mg/kg) significantly reduces the number of avoidance response (** $p<0.01$, n=6 per group, paired t-test). Experimental procedure was the same as in Example 12.

Example 15

Restoration of Novel Object Recognition for Compound 5-184

Figure 7:
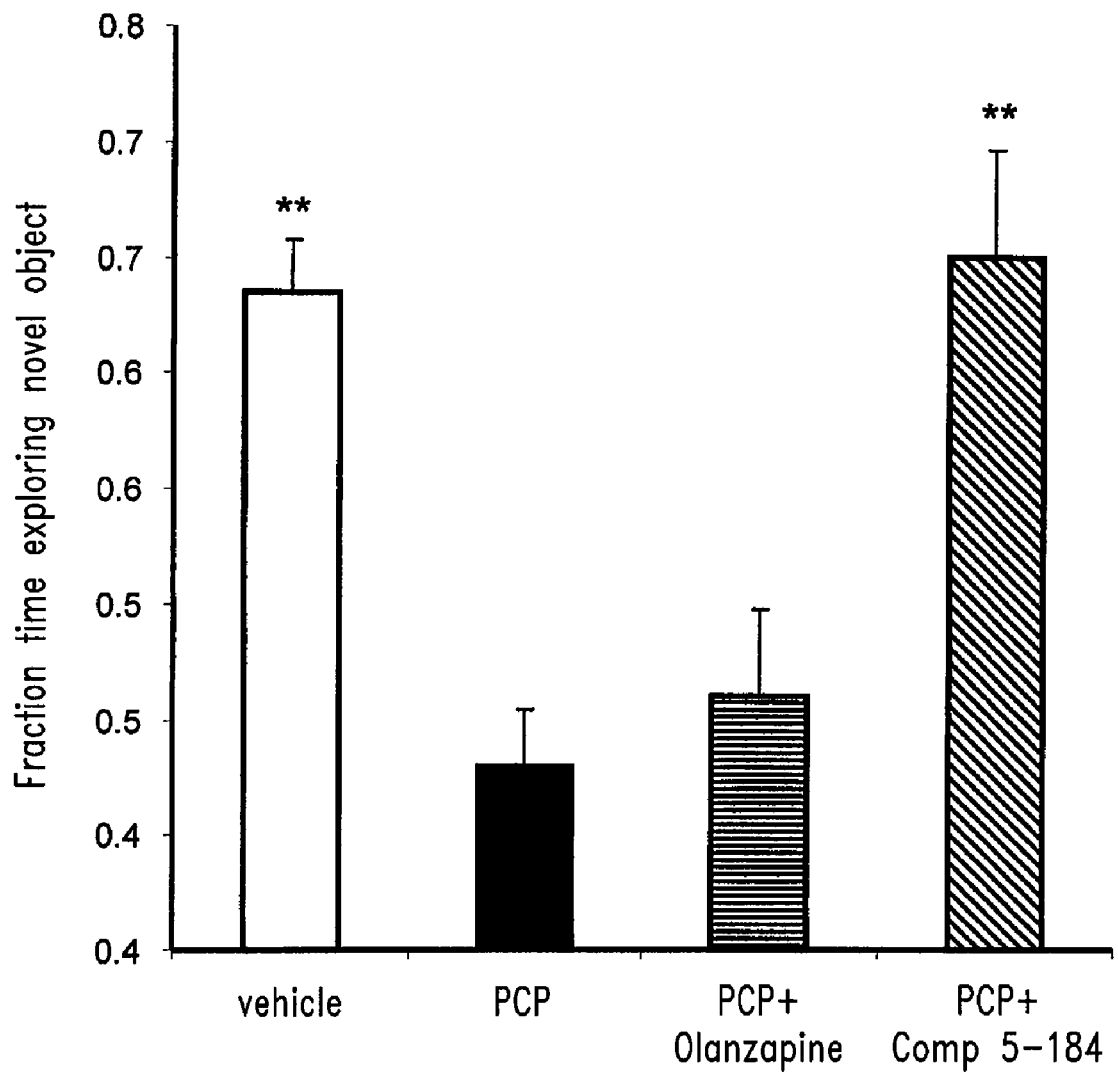
FIG. 7 illustrates that PCP (5 mg/kg) disrupts novel object recognition, and that compound 5-184 (10 mg/kg) is able to restore performance in this test. In contrast, olanzapine (1 mg/kg) is unable to restore this PCP-disrupted behavior (**$p<0.01$ when compared to PCP-treated group, n=8 per group, ANOVA with post-hoc Bonferroni test).

Compound 5-184 (Table 3) was found to restore PCP-disrupted novel object recognition as shown in FIG. 7. C57BL/6 male mice were injected with 10 μL/g of vehicle, PCP (5 mg/kg) or PCP+compound (10 mg/kg) via i.p. Twenty minutes after injection, the mice were presented with and allowed to explore two identical objects for 30 minutes. At the end of the exploration period, the objects were removed. Twenty-four hours later, each mouse was presented with a pair of objects, one familiar and one novel, and the time exploring each object was measured for 4 minutes starting from the first approach to either object. FIG. 7 shows that PCP (5 mg/kg) disrupted novel object recognition, that compound 5-184 (10 mg/kg) was able to restore novel object recognition performance, and that olanzapine (1 mg/kg) was unable to restore novel object recognition performance (** $p<0.01$ when compared to PCP-treated group, n=8 per group, ANOVA with post-hoc Bonferroni test).

It will be appreciated that, although specific embodiments of the invention have been described herein for purposes of illustration, various modifications may be made without departing from the spirit and scope of the invention. Accordingly, the invention is not limited except as by the appended claims.

We claim:
1. A compound having the following structure (IVg):

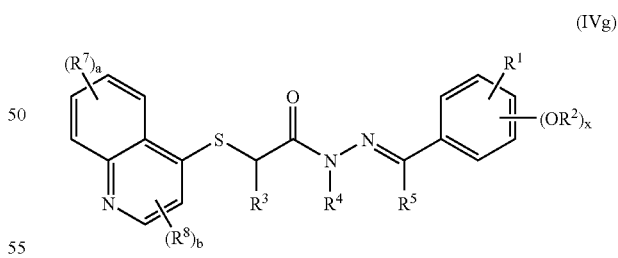

or a pharmaceutically acceptable salt or stereoisomer thereof, wherein:
  a is 1, 2, 3 or 4;
  b is 1 or 2;
  x is 1, 2 or 3 with the proviso that when x is 1, $R^1$ is not a single methyl substituent;
  $R^1$ represents 1 or 2 substitutents independently halogen, $C_{1-6}$alkyl, —$CHF_2$ or —$CF_3$;
  $R^2$ is at each occurrence the same or different and independently, hydrogen, $C_{1-6}$alkyl, benzyl, —CH$_2$CONH$_2$, —CHF$_2$, —CF$_3$, or any two R$^2$ groups may be taken together to form a C$_{1-6}$alkanediyl;

R$^3$, R$^4$ and R$^5$ are the same or different and independently hydrogen or C$_{1-6}$alkyl; and R$^7$ and R$^8$ are the same or different and independently hydrogen, halogen, C$_{1-6}$alkyl, —O(C$_{1-6}$alkyl), C$_{1-6}$haloalkyl or nitro.

2. The compound of claim 1 wherein R$^3$, R$^4$ and R$^5$ are hydrogen.

3. The compound of claim 1 wherein R$^7$ is hydrogen, R$^8$ is —CH$_3$, a is 1, b is 1 and the compound has the following structure:

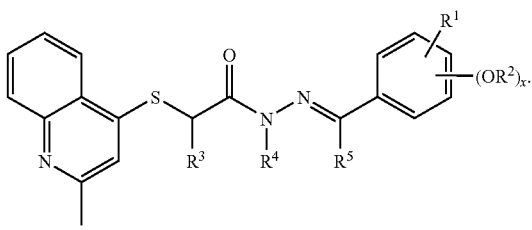

4. A pharmaceutical composition comprising a compound of claim 1 and a pharmaceutically acceptable carrier or diluent.

5. A compound having the following structure (IVa):

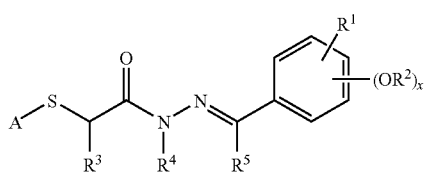

(IVa)

or a pharmaceutically acceptable salt or stereoisomer thereof, wherein:

A is

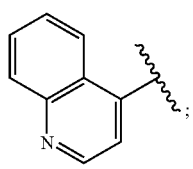

x is 3 and the —OR$^2$ groups are located at the 3, 4 and 5 positions;

R$^1$ is absent;

R$^2$ is at each occurrence the same or different and independently hydrogen, C$_{1-6}$alkyl, —C(=O)(C$_{1-6}$alkyl), benzyl, —CH$_2$CONH$_2$, —CHF$_2$ or —CF$_3$; and R$^3$, R$^4$ and R$^5$ are hydrogen.

6. The compound of claim 5 wherein R$^2$ is at each occurrence the same or different and independently C$_{1-6}$alkyl or —CHF$_2$ or —CF$_3$.

7. A pharmaceutical composition comprising a compound of claim 5 and a pharmaceutically acceptable carrier or diluent.

8. A compound having the following structure (IVa):

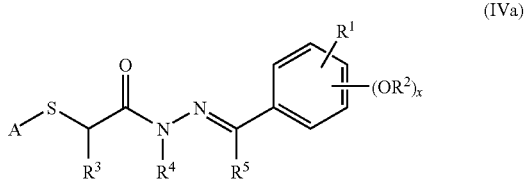

(IVa)

or a pharmaceutically acceptable salt or stereoisomer thereof, wherein:

A is

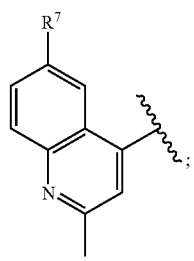

x is 2 or 3 and two of the —OR$^2$ groups are located at the 3 and 4 positions;

R$^1$ is absent;

R$^2$ is at each occurrence the same or different and independently C$_{1-6}$alkyl, —CHF$_2$ or —CF$_3$;

R$^3$, R$^4$ and R$^5$ are hydrogen; and

R$^7$ is —O(C$_{1-6}$alkyl).

9. A pharmaceutical composition comprising a compound of claim 8 and a pharmaceutically acceptable carrier or diluent.

10. A compound having the following structure (IVg):

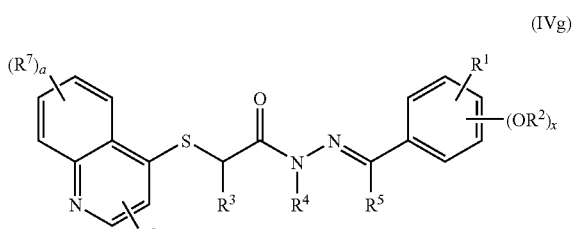

(IVg)

or a pharmaceutically acceptable salt or stereoisomer thereof, wherein:

x is 1, 2 or 3;

a is 1;

b is 0;

R$^1$ is absent or represents 1, 2, or 3 substituents that are the same or different and independently halogen, C$_{1-6}$alkyl, —CHF$_2$, —CF$_3$, —CH$_2$NH$_2$, —CH$_2$NH (C$_{1-6}$alkyl) or —CH$_2$N(C$_{1-6}$alkyl)$_2$;

R² is at each occurrence the same or different and independently hydrogen, $C_{1-6}$alkyl, —C(=O)($C_{1-6}$alkyl), benzyl, —$CH_2CONH_2$, —$CHF_2$ or —$CF_3$;

R³, R⁴ and R⁵ are hydrogen; and

R⁷ is halogen or $C_{1-6}$haloalkyl.

11. The compound of claim 10 wherein R² is at each occurrence the same or different and independently $C_{1-6}$alkyl, —$CHF_2$ or —$CF_3$.

12. The compound of claim 10 wherein R¹ is absent or represents 1, 2, or 3 substituents that are the same or different and independently halogen, $C_{1-6}$alkyl, —$CHF_2$ or —$CF_3$.

13. A pharmaceutical composition comprising a compound of claim 10 and a pharmaceutically acceptable carrier or diluent.

* * * * *